United States Patent
Falkenstein et al.

(10) Patent No.: US 9,481,706 B2
(45) Date of Patent: Nov. 1, 2016

(54) PURIFICATION OF NON-GLYCOSYLATED POLYPEPTIDES

(71) Applicant: Hoffmann-La Roche Inc., Nutley, NJ (US)

(72) Inventors: Roberto Falkenstein, Munich (DE); Birgit Weydanz, Penzberg (DE); Nicole Fuehrler, Schlehdorf (DE); Claudia Giessel, Bad Toelz (DE); Sybille Gabel, Peiting (DE); Adelbert Grossmann, Eglfing (DE); Friederike Hesse, Munich (DE); Marc Pompiati, Penzberg (DE); Andreas Schaubmar, Penzberg (DE); Brigitte Kraemer, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/246,783

(22) Filed: Apr. 7, 2014

(65) Prior Publication Data

US 2014/0220633 A1    Aug. 7, 2014

Related U.S. Application Data

(63) Continuation of application No. 13/624,091, filed on Sep. 21, 2012, now abandoned, which is a continuation of application No. 12/811,397, filed as application No. PCT/EP2009/000192 on Jan. 15, 2009, now abandoned.

(30) Foreign Application Priority Data

Jan. 18, 2008    (EP) .................................... 08000884

(51) Int. Cl.

| | |
|---|---|
| C07K 1/36 | (2006.01) |
| C07K 1/107 | (2006.01) |
| C07K 1/16 | (2006.01) |
| C07K 1/18 | (2006.01) |
| C07K 1/20 | (2006.01) |
| C07K 1/22 | (2006.01) |

(52) U.S. Cl.
CPC .............. *C07K 1/1077* (2013.01); *C07K 1/16* (2013.01); *C07K 1/18* (2013.01); *C07K 1/20* (2013.01); *C07K 1/22* (2013.01); *C07K 1/36* (2013.01)

(58) Field of Classification Search
None
See application file for complete search history.

(56) References Cited

U.S. PATENT DOCUMENTS

| | | |
|---|---|---|
| 5,696,238 A | 12/1997 | Haigwood et al. |
| 2005/0266465 A1 | 12/2005 | Patten et al. |

FOREIGN PATENT DOCUMENTS

| | | |
|---|---|---|
| DE | 4329756 | 3/1995 |
| JP | H07135992 A | 5/1995 |
| JP | H07322887 A | 12/1995 |
| JP | 2007533651 A | 11/2007 |
| JP | 2008500273 A | 1/2008 |
| KR | 2002/0080108 | 10/2002 |
| WO | 2003/102132 | 12/2003 |
| WO | 2005/94960 A1 | 10/2005 |
| WO | 2006/101441 | 9/2006 |
| WO | 2007/016250 | 2/2007 |
| WO | 2007/041713 | 4/2007 |
| WO | 2007/075283 | 7/2007 |

OTHER PUBLICATIONS

Rege, K. et al., "High-Throughput Process Development for Recombinant Protein Purification" Biotechnology Bioengineering 93:618-630 ( 2006).
(International Search Report PCT/EP2009/000192 Dec. 3, 2009).
Cromwell, O. et al., "Transition of recombinant allergens from bench to clinical applications" Methodas:A Companion to Methods in Enzymology (XP004488981), 32(3):300-312 ( 2004).
Bernardi, "Chromatography of Proteins on Hydroxyapatite" Method in Enzymology 27:471-479 ( 1973).
Fahrner et al., "Industrial Purification of Pharmaceutical Antibodies: Development, Operation, and Validation of Chromatography Processes" Biotechnol Genet Eng 18:301-327 ( 2001).
Stein et al., "Cation Exchange Chromatography in Antibody Purification: pH Screening for Optimised Binding and HCP Removal" Journal of Chromatography B, 848, (Mar. 12, 2007), pp. 151-158.

*Primary Examiner* — Nashaat Nashed
(74) *Attorney, Agent, or Firm* — James E. Nesbitt

(57) ABSTRACT

The current invention reports a method for the purification of a not-glycosylated, heterologous polypeptide, which has been recombinantly produced in a prokaryotic cell, wherein the method comprises three chromatography steps of which the first chromatography step selected from i) hydrophobic charge induction chromatography, or ii) hydrophobic interaction chromatography, or iii) affinity chromatography, or iv) ion exchange chromatography, the second chromatography step is selected from i) anion exchange chromatography, or ii) cation exchange chromatography, or iii) hydroxylapatite chromatography, or iv) hydrophobic interaction chromatography, and the a third chromatography step is selected from i) hydrophobic charge induction chromatography, or ii) anion exchange chromatography, or iii) cation exchange chromatography, or iv) hydrophobic interaction chromatography, whereby the first chromatography step is an affinity chromatography in case of polypeptides capable of interacting with metal ligands, the second chromatography step is not a hydroxylapatite chromatography step in case of polypeptides with an isoelectric point below 6.0, and the third chromatography step can be performed in flow-through mode with polypeptides having a low or high isoelectric point.

10 Claims, 12 Drawing Sheets

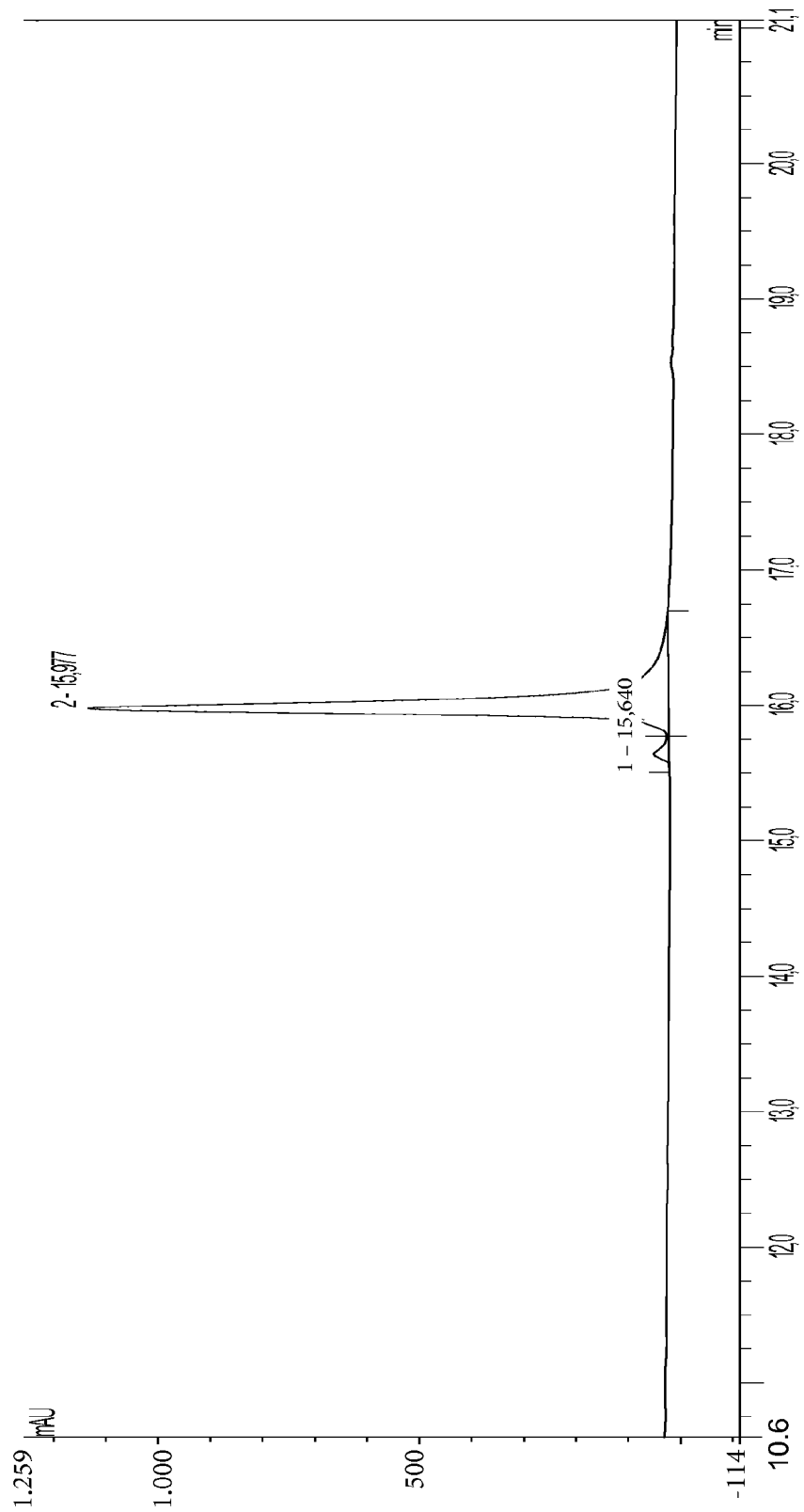

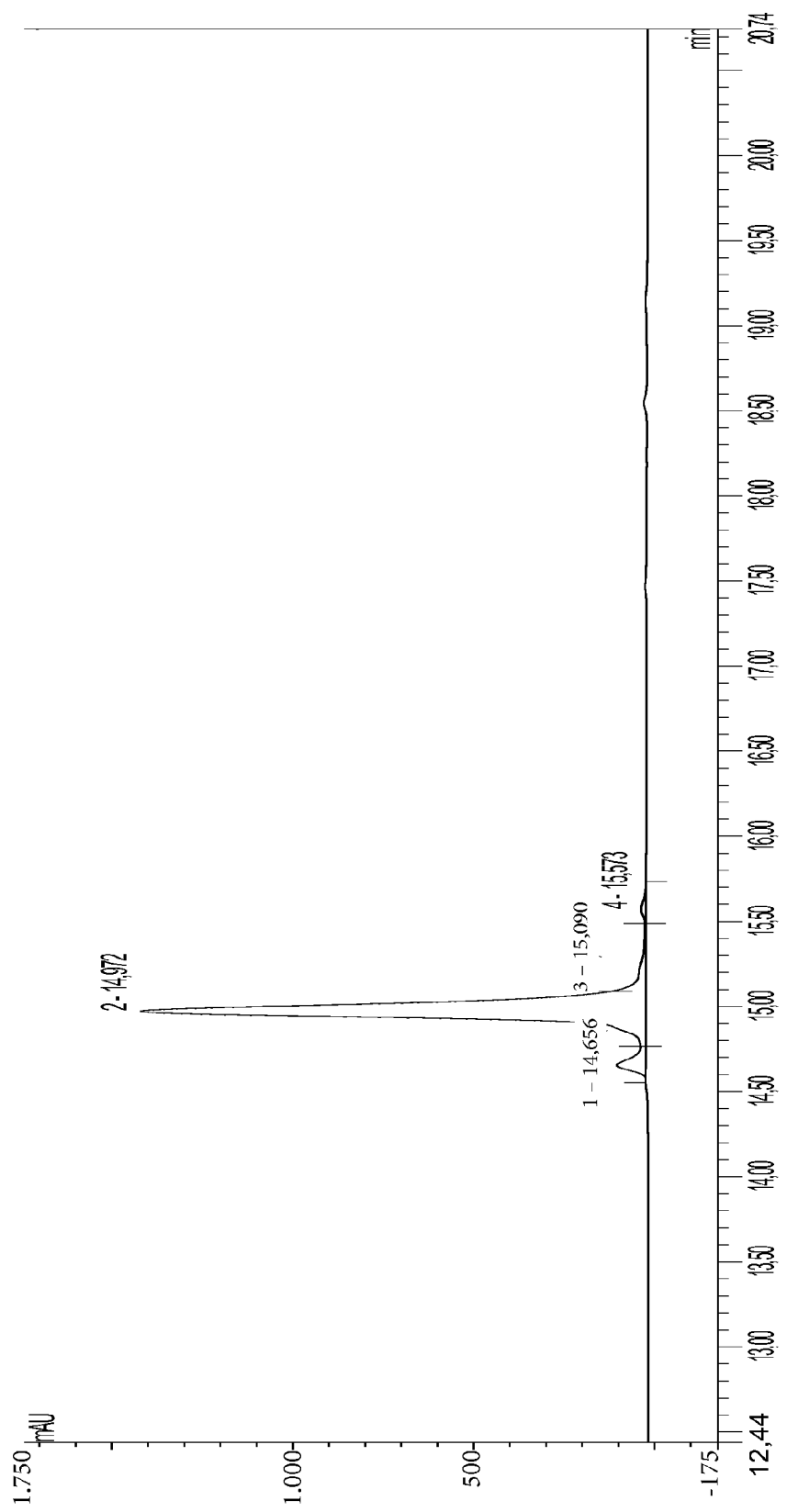

PURIFICATION OF NON-GLYCOSYLATED POLYPEPTIDES

This application is a continuation of U.S. patent application Ser. No. 13/624,091, filed 21 Sep. 2012, which is a continuation of U.S. patent application Ser. No. 12/811,397, filed 1 Jul. 2010, which is a National Stage application of International Patent Application No. PCT/EP2009/000192, filed under 35 USC 371 on 15 Jan. 2009, which claims the benefit of European Patent Application No. EP08000884.0, filed 18 Jan. 2008, each of which is incorporated by reference herein in its entirety.

FIELD OF THE INVENTION

The current invention relates to the field of polypeptide purification. A general method for the purification of non-glycosylated polypeptides with a combination of three chromatographic steps is reported.

BACKGROUND OF THE INVENTION

Proteins play an important role in today's medical portfolio. For human application every pharmaceutical substance has to meet distinct criteria. To ensure the safety of biopharmaceutical agents to humans nucleic acids, viruses, and host cell proteins, which would cause severe harm, have to be removed especially. To meet the regulatory specification one or more purification steps have to follow the manufacturing process. Among other purity, throughput, and yield play an important role in determining an appropriate purification process.

Different methods are well established and widespread used for protein purification, such as affinity chromatography with thiophilic ligands, Cu-chelate, or microbial proteins (e.g., protein A or protein G affinity chromatography), ion exchange chromatography (e.g., cation exchange, anion exchange, and mixed-mode exchange), thiophilic adsorption, hydrophobic interaction or aromatic adsorption chromatography, size exclusion chromatography, and electrophoretical methods (such as gel electrophoresis, capillary electrophoresis) (Vijayalakshmi, M. A., Appl. Biochem. Biotech. 75 (1998) 93-102).

Recombinant polypeptides can be produced e.g., by prokaryotic cells such as *E. coli*. The recombinantly produced polypeptide accounts for the majority of the prokaryotic cell's polypeptide content and is often deposited as insoluble aggregate, i.e., as a so called inclusion body, within the prokaryotic cell. For the isolation of the recombinant polypeptide the cells have to be disintegrated and the recombinant polypeptide contained in the inclusion bodies has to be solubilized after the separation of the inclusion bodies from the cell debris. For the solubilization chaotropic reagents, such as urea or guanidinium hydrochloride, are used. To cleave disulfide bonds reducing agents, especially under alkaline conditions, such as dithioerythriol, dithiothreitol, or β-mercaptoethanol are added. After the solubilization of the aggregated polypeptide the globular structure of the recombinant polypeptide, which is essential for the biological activity, has to be reestablished. During this so called renaturation process the concentration of the denaturating agents is slowly reduced, e.g., by dialysis against a suited buffer, which allows the denatured polypeptide to refold into its biologically active structure. After the renaturation is the recombinant polypeptide purified to a purity acceptable for the intended use. For example, for the use as a therapeutic protein a purity of more than 90% has to be established. Recombinantly produced polypeptides obtained from *E. coli* are normally accompanied by nucleic acids, endotoxins, polypeptides from the producing cell, and not-renaturated recombinant polypeptides.

With the number of different chromatographic methods available a multitude of combinations has to be tested in order to find a suitable purification process. In these combinations different sequences and even different numbers of chromatographic methods may be used. Thus, a method for determining a suitable sequence of chromatographic steps for the purification of a non-glycosylated polypeptide is desirable.

In WO 2007/075283 a multi step system and methods of target molecule purification are reported. Methods for purifying compounds comprising a protein of interest are reported in WO 2007/016250. A process for purifying a recombinant protein including one or a few procedural steps only is reported in WO 2006/101441. Rege et al. (Rege, K., Biotechnol. Bioeng. 93 (2006) 618-630) report a high-throughput process development for recombinant protein purification. In KR 2002/080108 a process for purifying human growth hormone from recombinant *E. coli* is reported.

SUMMARY OF THE INVENTION

The first aspect of the current invention is a method for the purification of a non-glycosylated, heterologous polypeptide, which has been recombinantly produced in a prokaryotic cell, wherein the method comprises the following three chromatography steps in the following order:
 a) a first chromatography step selected from
  i) hydrophobic charge induction chromatography,
  ii) hydrophobic interaction chromatography,
  iii) affinity chromatography, or
  iv) ion exchange chromatography,
 b) a second chromatography step selected from
  i) anion exchange chromatography,
  ii) cation exchange chromatography,
  iii) hydroxylapatite chromatography,
  iv) hydrophobic interaction chromatography, or
  v) hydrophobic charge induction chromatography,
 c) a third chromatography step selected from
  i) hydrophobic charge induction chromatography,
  ii) anion exchange chromatography,
  iii) cation exchange chromatography, or
  iv) hydrophobic interaction chromatography,
 whereby
  the first chromatography step is an affinity chromatography in case of polypeptides capable of interacting with metal ligands,
  the second chromatography step is not a hydroxylapatite chromatography step in case of polypeptides with an isoelectric point below 6.0,
  the third chromatography step can be performed in flow-through mode with polypeptides having a low or high isoelectric point,
  optionally the third chromatography step can be used for concentration of the polypeptide,
 and the purified non-glycosylated, heterologous polypeptide is obtained after step c).

The method according to the invention comprises at least three chromatography steps, whereby for each step a chromatography material can be selected independently of the chromatography material selected for the previous step or for the following step, whereby only the given provisos have to be taken into account. Thus, the method according to the invention provides for a flexible and exchangeable sequence of chromatography steps for the purification of a non-glycosylated polypeptide, whereby the obtained purity after subjecting the non-glycosylated polypeptide to the method according to the invention is comparable independently of the selected chromatography step sequence.

In one embodiment is the prokaryotic cell an *E. coli* cell. In another embodiment is the affinity chromatography a metal chelating chromatography. In a further embodiment comprises the method an additional step either after step a) or after step b) or after step c) which is d) PEGylating said polypeptide. In one embodiment said steps a) and b) are cation exchange chromatography. In still a further embodiment is the non-glycosylated, heterologous polypeptide selected from growth factor agonists or antagonists, or interferons or interferon variants.

A second aspect of the current invention is a method for the recombinant production of a non-glycosylated heterologous polypeptide in a prokaryotic cell, wherein the method comprises the following steps:
 a) cultivating a prokaryotic cell comprising a nucleic acid encoding a heterologous polypeptide under conditions suitable for the expression of the heterologous polypeptide,
 b) recovering the heterologous polypeptide from the culture medium or the prokaryotic cells,
 c) purifying the heterologous polypeptide with a method according to the invention and thereby obtaining a non-glycosylated heterologous polypeptide.

In one embodiment the methods according to the invention are characterized in that at least two different sequences of three chromatographic steps yield a purified non-glycosylated, heterologous polypeptide with comparable purity. In one embodiment the third chromatography step can be performed in flow-through mode with polypeptides having a low, i.e., 6.0 or lower, or high, i.e., 8.0 or higher, isoelectric point.

DETAILED DESCRIPTION OF THE INVENTION

General chromatographic methods and their use are known to a person skilled in the art. See for example, Chromatography, 5$^{th}$ edition, Part A: Fundamentals and Techniques, Heftmann, E. (ed), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991), Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; Current Protocols in Molecular Biology, Ausubel, F. M., et al. (eds)., John Wiley & Sons, Inc., New York; or Freitag, R., Chromatographical processes in the downstream processing of (recombinant) proteins, Meth. Biotechnol. 24 (2007) 421-453 (Animal cell biotechnology 2$^{nd}$ Edition).

Methods for purifying polypeptides are well established and widespread used. They are employed either alone or in combination. Such methods are, for example, affinity chromatography using thiol ligands with complexed metal ions (e.g. with Ni(II)- and Cu(II)-affinity material) or microbial-derived proteins (e.g. protein A or protein G affinity chromatography), ion exchange chromatography (e.g. cation exchange (carboxymethyl resins), anion exchange (amino ethyl resins) and mixed-mode exchange chromatography), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), size exclusion chromatography, and preparative electrophoretic methods (such as gel electrophoresis, capillary electrophoresis) (Vijayalakshmi, M. A., Appl. Biochem. Biotech. 75 (1998) 93-102).

The term "buffered" as used within this application denotes a solution in which changes of pH due to the addition or release of acidic or basic substances is leveled by a buffer substance. Any buffer substance resulting in such an effect can be used. Preferably pharmaceutically acceptable buffer substances are used, such as e.g., phosphoric acid or salts thereof, acetic acid or salts thereof, citric acid or salts thereof, morpholine or salts thereof, 2-(N-morpholino) ethanesulfonic acid or salts thereof, histidine or salts thereof, glycine or salts thereof, or Tris(hydroxymethyl)aminomethane (TRIS) or salts thereof. Especially preferred are phosphoric acid or salts thereof, or acetic acid or salts thereof, or citric acid or salts thereof, or histidine or salts thereof. Optionally the buffered solution may comprise an additional salt, such as e.g., sodium chloride, sodium sulphate, potassium chloride, potassium sulfate, sodium citrate, or potassium citrate.

The term "membrane" as used within this application denotes both a microporous or macroporous membrane. The membrane itself is composed of a polymeric material such as, e.g., polyethylene, polypropylene, ethylene vinyl acetate copolymers, polytetrafluoroethylene, polycarbonate, poly vinyl chloride, polyamides (nylon, e.g. Zetapore™, N$_{66}$ Posidyne™), polyesters, cellulose acetate, regenerated cellulose, cellulose composites, polysulphones, polyethersulfones, polyarylsulphones, polyphenylsulphones, polyacrylonitrile, polyvinylidene fluoride, non-woven and woven fabrics (e.g. Tyvek®), fibrous material, or of inorganic material such as zeolithe, $SiO_2$, $Al_2O_3$, $TiO_2$, or hydroxylapatite.

The term "chromatography material" as used within this application denotes on the one hand a solid material that can be used without further modification as chromatography material, such as hydroxylapatite or affinity chromatography material, and also material comprising a bulk core material to which chromatographical functional groups are attached, preferably by covalent bonds. The bulk core material is understood to be not involved in the chromatography process, i.e., the interaction between the polypeptide to be separated and the chromatographical functional groups of the chromatography material. It is merely providing a three dimensional framework to which the chromatographical functional groups are attached and which ensures that the solution containing the substance to be separated can access the chromatographical functional group. Preferably said bulk core material is a solid phase. Thus, preferably said "chromatography material" is a solid phase to which chromatographical functional groups are attached, preferably by covalent bonds. Preferably said "chromatographical functional group" is an ionizable hydrophobic group, or a hydrophobic group, or a complex group in which different chromatographical functional groups are combined in order to bind only a certain type of polypeptide, or a covalently bound charged group.

A "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; zeolites and other porous substances. A solid phase may be a stationary component, such as a packed chromatography column, or may be a non-stationary component, such as beads and microparticles. Such particles include polymer particles such as polystyrene and poly(methylmethacrylate); gold particles such as gold nanoparticles and gold colloids; and ceramic particles such as silica, glass, and metal oxide particles. See, for example, Martin, C. R., et al., Analytical Chemistry-News & Features, May 1 (1998) 322A-327A.

The terms "hydrophobic charge induction chromatography" or "HCIC", which can be used interchangeably within this application, denote a chromatography method which employs a "hydrophobic charge induction chromatography material". A "hydrophobic charge induction chromatography material" is a chromatography material which comprises chromatographical function groups which can in one pH range form hydrophobic bonds to the substance to be separated and which are charged either positively or negatively in other pH ranges, i.e., HCIC uses ionizable hydrophobic groups as chromatographical functional group. Generally the polypeptide is bound to the hydrophobic charge induction material under neutral pH conditions and recovered afterwards by the generation of charge repulsion by a change of the pH value. An exemplary "hydrophobic charge induction chromatography materials" is BioSepra MEP or HEA Hypercel (Pall Corp., USA).

The terms "hydrophobic interaction chromatography" or "HIC", which can be used interchangeably within this application, denote a chromatography method in which a "hydrophobic interaction chromatography material" is employed. A "hydrophobic interaction chromatography material" is a chromatography material to which hydrophobic groups, such as butyl-, octyl-, or phenyl-groups, are bound as chromatographical functional groups. The polypeptides are separated depending on the hydrophobicity of their surface exposed amino acid side chains, which can interact with the hydrophobic groups of the hydrophobic interaction chromatography material. The interactions between polypeptides and the chromatography material can be influenced by temperature, solvent, and ionic strength of the solvent. A temperature increase e.g. supports the interaction between the polypeptide and the hydrophobic interaction chromatography material as the motion of the amino acid side chains increases and hydrophobic amino acid side chains buried inside the polypeptide at lower temperatures become accessible. Also is the hydrophobic interaction promoted by kosmotropic salts and decreased by chaotropic salts. "Hydrophobic interaction chromatography materials" are e.g., Phenylsepharose CL-4B, 6 FF, HP, Phenyl Superose, Octylsepharose CL-4B, 4 FF, and Butylsepharose 4 FF (all available from Amersham Pharmacia Biotech Europe GmbH, Germany), which are obtained via glycidyl-ether coupling to the bulk material.

The term "affinity chromatography" as used within this application denotes a chromatography method which employs an "affinity chromatography material". In an affinity chromatography the polypeptides are separated based on their biological activity or chemical structure depending of the formation of electrostatic interactions, hydrophobic bonds, and/or hydrogen bond formation to the chromatographical functional group. To recover the specifically bound polypeptide from the affinity chromatography material either a competitor ligand is added or the chromatography conditions, such as pH value, polarity or ionic strength of the buffer are changed. An "affinity chromatography material" is a chromatography material which comprises a complex chromatographical functional group in which different single chromatographical functional groups are combined in order to bind only a certain type of polypeptide. This chromatography material specifically binds a certain type of polypeptide depending on the specifty of its chromatographical functional group. Exemplary "affinity chromatographical materials" are a "metal chelating chromatography material" such as Ni(II)-NTA or Cu(II)-NTA containing materials, for the binding of fusion polypeptides containing a hexahistidine tag or polypeptides with a multitude of surface exposed histidine, cysteine, and/or tryptophane residues, or an "antibody binding chromatography material" such a protein A, or an "enzyme binding chromatography material" such as chromatography materials comprising enzyme substrate analogues, enzyme cofactors, or enzyme inhibitors as chromatographical functional group, or a "lectin binding chromatography material" such as chromatography materials comprising polysaccharides, cell surface receptors, glycoproteins, or intact cells as chromatographical functional group.

The term "metal chelating chromatography" as used within this application denotes a chromatography method which employs a "metal chelating chromatography material". Metal chelating chromatography is based on the formation of chelates between a metal ion, such as Cu(II), Ni(II) or Zn(II), which is bound to a bulk material as chromatographical functional groups, and electron donor groups of surface exposed amino acid side chains of polypeptides, especially with imidazole containing side chains and thiol group containing side chains. The chelate is formed at pH values at which those side chains are at least partly not protonated. The bound polypeptide is recovered from the chromatography material by a change in the pH value, i.e., by protonation. Exemplary "metal chelating chromatography materials" are HiTrap Chelating HP (Amersham Pharmacia Biotec Europe GmbH, Germany), or Fraktogel EMD (EMD Chemicals Inc, USA).

The term "ion exchange chromatography" as used within this application denotes a chromatography method which employs an "ion exchange chromatography material". The term "ion exchange chromatography material" encompasses depending whether a cation is exchanged in a "cation exchange chromatography" a "cation exchange chromatography material" or an anion is exchanged in an "anion exchange chromatography" an "anion exchange chromatography material". The term "ion exchange chromatography material" as used within this application denotes an immobile high molecular weight solid phase that carries covalently bound charged groups as chromatographical functional groups. For overall charge neutrality not covalently bound counter ions are associated therewith. The "ion exchange chromatography material" has the ability to exchange its not covalently bound counter ions for similarly charged ions of the surrounding solution. Depending on the charge of its exchangeable counter ions the "ion exchange chromatography material" is referred to as "cation exchange chromatography material" or as "anion exchange chromatography material". Further depending on the nature of the charged group the "ion exchange chromatography material" is referred to as, e.g., in the case of cation exchange chromatography materials with sulfonic acid groups (S), or carboxymethyl groups (CM). Depending on the chemical nature of the charged group the "ion exchange chromatography material" can additionally be classified as strong or weak ion exchange chromatography material, depending on the strength of the covalently bound charged substituent. For example, strong cation exchange chromatography materials have a sulfonic acid group as chromatographical functional group and weak cation exchange chromatography materials have a carboxylic acid group as chromatographical functional group. "Cation exchange chromatography materials", for example, are available under different names from a multitude of companies such as, e.g., Bio-Rex, Macro-Prep CM (available from Biorad Laboratories, Hercules, Calif., USA), weak cation exchanger WCX 2 (available from Ciphergen, Fremont, Calif., USA), Dowex® MAC-3 (available from Dow chemical company—liquid separations, Midland, Mich., USA), Mustang C (available from Pall Corporation, East Hills, N.Y., USA), Cellulose CM-23, CM-32, CM-52, hyper-D, and partisphere (available from Whatman plc, Brentford, UK), Amberlite® IRC 76, IRC 747, IRC 748, GT 73 (available from Tosoh Bioscience GmbH, Stuttgart, Germany), CM 1500, CM 3000 (available from BioChrom Labs, Terre Haute, Ind., USA), and CM-Sepharose™ Fast Flow (available from GE Healthcare—Amersham Biosciences Europe GmbH, Freiburg, Germany).

The term "hydroxylapatite chromatography" as used within this application denotes a chromatography method that employs a certain form of calcium phosphate as chromatography material. Exemplary hydroxylapatite chromatography materials are Bio-Gel HT, Bio-Gel HTP, Macro-Prep Ceramic (available from Biorad Laboratories), Hydroxylapatite Type I, Type II, HA Ultrogel (Sigma Aldrich Chemical Corp., USA), Hydroxylapatite Fast Flow and High Resolution (Calbiochem), or TSK gel HA-1000 (Tosoh Haas Corp., USA).

A "polypeptide" is a polymer of amino acid residues joined by peptide bonds, whether produced naturally or synthetically. Polypeptides of less than about 20 amino acid residues are referred to as "peptides." A "protein" is a molecule comprising one or more polypeptide chains whereof at least one comprises 100 or more amino acid residues. Polypeptides and protein may also comprise non-amino acid components, such as carbohydrate groups. Carbohydrate groups and other non-amino acid components may be added by the cell in which the polypeptide or protein is produced, and will vary with the type of cell. Polypeptides and proteins are defined herein in terms of their amino acid backbone structures; substituents such as carbohydrate groups are generally not specified, but may be present nonetheless.

The terms "antibody" and "immunoglobulin", which can be used interchangeably within this application, denote a molecule generally comprising two light chains and two heavy chains. Each of the heavy and light chains comprises a variable region (generally the amino terminal portion of the chain) which contains specific binding regions (CDR, complementary determining region) which interacts with the antigen. Each of the heavy and light chains also comprises a constant region (generally, the carboxyl terminal portion of the chains) which may mediate the binding of the immunoglobulin to host tissues or factors including various cells of the immune system, some phagocytic cells and a first component (C1q) of the classical complement system. Typically, the light and heavy chains of an immunoglobulin are complete chains, each consisting essentially of a variable region and a complete constant region. Generally a light chain comprises a light chain variable domain, a hinge region, and a light chain constant domain, whereas a heavy chain comprises a heavy chain variable domain, a hinge region, and a heavy chain constant domain consisting of a $C_H1$ domain, a $C_H2$ domain, a $C_H3$ domain, and optionally a $C_H4$ domain. Antibodies may exist in a variety of forms, including, for example, Fv, Fab, and $F(ab)_2$ as well as single chains (e.g., Huston, J. S., et al., Proc. Natl. Acad. Sci. USA 85 (1988) 5879-5883; Bird et al., Science 242 (1988) 423-426; and, in general, Hood et al., Immunology, Benjamin N.Y., 2nd edition (1984) and Hunkapiller and Hood, Nature 323 (1986) 15-16). Depending on the amino acid sequence of the constant region of the heavy chain are immunoglobulins assigned to different classes: IgA, IgD, IgE, IgG, and IgM. Some of these classes are further divided into subclasses (isotypes), i.e., IgG in IgG1, IgG2, IgG3, and IgG4, or IgA in IgA1 and IgA2. According to the immunoglobulin class to which an immunoglobulin belongs the heavy chain constant regions of immunoglobulins are called α (IgA), δ (IgD), ε (IgE), γ (IgG), and μ (IgM), respectively.

The term "bind-and-elute mode" and grammatical equivalents thereof as used in the current invention denotes an operation mode of a chromatography method, in which a solution containing a substance of interest is brought in contact with a stationary phase, preferably a solid phase, whereby the substance of interest binds to the stationary phase. As a result the substance of interest is retained on the stationary phase whereas substances not of interest are removed with the flow-through or the supernatant. The substance of interest is afterwards eluted from the stationary phase in a second step and thereby recovered from the stationary phase with an elution solution. This does not necessarily denote that 100% of the substances not of interest are removed but essentially 100% of the substances not of interest are removed, i.e., at least 50% of the substances not of interest are removed, preferably at least 75% of the substances not of interest are removed, preferably at least 90% of the substances not of interest are removed, preferably more than 95% of the substances not of interest are removed.

The term "flow-through mode" and grammatical equivalents thereof as used within the current invention denotes an operation mode of a chromatography method, in which a solution containing a substance of interest is brought in contact with a stationary phase, preferably a solid phase, whereby the substance of interest does not bind to that stationary phase. As a result the substance of interest is obtained either in the flow-through or the supernatant. Substances not of interest, which were also present in the solution, bind to the stationary phase and are removed from the solution. This does not necessarily denote that 100% of the substances not of interest are removed from the solution but essentially 100% of the substances not of interest are removed, i.e., at least 50% of the substances not of interest are removed from the solution, preferably at least 75% of the substances not of interest are removed from the solution, preferably at least 90% of the substances not of interest are removed from the solution, preferably more than 95% of the substances not of interest are removed from the solution.

The terms "continuous elution" and "continuous elution method", which are used interchangeably within this application, denote a chromatography method wherein e.g., the concentration of a substance causing elution, i.e., the dissolution of a bound substance from a chromatography material, is raised or lowered continuously, i.e., the concentration is changed by a sequence of small steps each not bigger than a change of 2%, preferably of 1%, of the concentration of the substance causing elution. In this "continuous elution" one or more conditions, for example the pH, the ionic strength, concentration of a salt, and/or the flow of a chromatography method, may be changed linearly, or changed exponentially, or changed asymptotically. Preferably the change is linear.

The terms "step elution" and "step elution method", which are used interchangeably within this application, denote a chromatography method wherein e.g., the concentration of a substance causing elution, i.e., the dissolution of a bound substance from a chromatography material, is raised or lowered at once, i.e., directly from one value/level to the next value/level. In this "step elution" one or more conditions, for example the pH, the ionic strength, concentration of a salt, and/or the flow of a chromatography method, is/are changed all at once from a first, e.g., starting, value to a second, e.g., final, value. The change in the step is bigger than a change of 5%, preferably of 10%, of the concentration of the substance causing elution. "Step elution" denotes that the conditions are changed incrementally, i.e., stepwise, in contrast to a linear change. In the "step elution method" is after each increase a new fraction collected. After each increase the conditions are maintained till the next step in the elution method.

An "isolated polypeptide" is a polypeptide that is essentially free from contaminating cellular components, such as carbohydrate, lipid, or other proteinaceous impurities associated with the polypeptide in nature. Typically, a preparation of an isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers, derivatized forms, not correctly folded forms, not correctly disulfide bridged forms, or scrambled forms.

"Heterologous DNA" or "heterologous polypeptide" refers to a DNA molecule or a polypeptide, or a population of DNA molecules or a population of polypeptides that do not exist naturally within a given cell. DNA molecules heterologous to a particular cell may contain DNA derived from the cell's species (i.e., endogenous DNA) so long as that cell's DNA is combined with non-cell's DNA (i.e., exogenous DNA). For example, a DNA molecule containing a non-cell's DNA segment encoding a polypeptide operably linked to a cell's DNA segment comprising a promoter is considered to be a heterologous DNA molecule. Conversely, a heterologous DNA molecule can comprise an endogenous structural gene operably linked with an exogenous promoter.

A peptide or polypeptide encoded by a non-cell's DNA molecule is a "heterologous" peptide or polypeptide.

It has now surprisingly been found that with the method according to the invention the purification of non-glycosylated polypeptides, which have been produced recombinantly by a prokaryotic cell, can be performed. It has been found that only a small defined number of a maximum of three chromatography steps is required and also that only a defined number of different chromatography methods have to be tested in order to establish a chromatographic purification process with allows the purification of a non-glycosylated, recombinantly produced polypeptide to a purity that allows the use of said non-glycosylated, recombinantly produced polypeptide for therapeutic purposes.

Therefore, the current invention provides in a first aspect a method for purifying a non-glycosylated, heterologous polypeptide, which has been recombinantly produced in a prokaryotic cell, comprising the following steps in the following order:

a) a first chromatography step selected from
  i) hydrophobic charge induction chromatography,
  ii) hydrophobic interaction chromatography,
  iii) affinity chromatography, or
  iv) ion exchange chromatography,
b) a second chromatography step selected from
  i) anion exchange chromatography,
  ii) cation exchange chromatography,
  iii) hydroxylapatite chromatography, or
  iv) hydrophobic interaction chromatography, or
  v) hydrophobic charge induction chromatography,
c) a third chromatography step selected from
  i) hydrophobic charge induction chromatography,
  ii) anion exchange chromatography,
  iii) cation exchange chromatography, or
  iv) hydrophobic interaction chromatography.

In one embodiment is the purified non-glycosylated, heterologous polypeptide obtained after step c) of the method according to the invention. Due to the different characteristics of different polypeptides, which are depending on its physical properties, such as e.g., the isoelectric point (Ip) or the distribution of surface exposed amino acid residues, not all chromatography methods are suited for all polypeptides. Therefore the following provisos apply to the method according to the invention:

the first chromatography step is an affinity chromatography or a hydrophobic charge induction chromatography in case of polypeptides capable of interacting with metal ligands, the second chromatography step is not a hydroxylapatite chromatography step in case of polypeptides with an isoelectric point below 6.0, the third chromatography step can be performed in flow-through mode with polypeptides having a low or high isoelectric point, optionally the third chromatography step can be used to concentrate the polypeptide solution.

The method according to the current invention will be exemplified in the following. These examples are only presented to exemplify the method according to the current invention but not to restrict the scope of the invention, which is presented in the appended claims.

IGF-1 Agonist

A first exemplary polypeptide is an IGF-1 agonist as reported e.g., in WO 2006/066891.

For the purification of the IGF-1 agonist a sequence of three chromatography steps according to the method according to the invention have been performed. The sequence comprises the chromatography steps:

1) hydrophobic charge induction chromatography (a-i),
2) hydroxylapatite chromatography (b-iii), and
3) hydrophobic charge induction chromatography (c-i).

This sequence fulfills the provisos for the method according to the invention as the polypeptide has a hexahistidine tag and an isoelectric point above 6.0.

The starting material had a purity of 50% (determined by HPLC) of the IGF-1 agonist. After performing the purification method according to the invention with the chromatography steps as outlined above a purity of more than 97% (determined by HPLC) has been obtained. All three chromatography steps have been performed in a bind-and-elute mode.

To show the versatility of the method according to the invention the IGF-1 agonist has also been purified with a different sequence of chromatography steps according to the method according to the invention which are:

1) hydrophobic interaction chromatography (a-ii),
2) cation exchange chromatography (b-ii), and
3) anion exchange chromatography (c-ii).

After performing the purification method according to the invention with the chromatography steps as outlined above a purity of 97% (determined by HPLC) has been obtained. The first and second chromatography steps have been performed in a bind-and-elute mode and the third chromatography step has been performed in flow-through-mode.

Thus, it has surprisingly been found that with different sequences of three chromatography steps the same molecule can be purified to a similar purity. Furthermore has been found that the final chromatography step can be performed in different elution modes, i.e., in a bind-and-elute mode or in a flow-through mode. Also has been found that the different chromatography steps can be performed either as step elution or as continuous elution.

Thus, another aspect of the current invention is a method for the purification of a polypeptide, especially of IGF-1 or an IGF-1 variant as reported in WO 2006/066891, comprising a sequence of three successive chromatography steps whereby the first chromatography step is a hydrophobic charge induction chromatography, the second chromatography step is selected from hydroxylapatite chromatography or cation exchange chromatography, and the third chromatography step is selected from hydrophobic charge induction chromatography or anion exchange chromatography.

Interferon

A second exemplary polypeptide is interferon alpha-2a (IFNα-2a) as reported e.g., in EP 0 043 980.

For the purification of the IFNα-2a a sequence of three chromatography steps according to the method according to the invention have been performed. The sequence comprises the chromatography steps:

1) hydrophobic charge induction chromatography (a-i),
2) anion exchange chromatography (b-ii), and
3) hydrophobic interaction chromatography (c-iv).

This sequence fulfills the provisos for the method according to the invention as the recombinantly produced IFNα-2a has no tag for the interaction with a metal chelating chromatography material and has an isoelectric point above 6.0.

The starting material had a purity of 49% (determined by HPLC). After performing the purification method according to the invention with the chromatography steps as outlined above a purity of more than 99% (determined by HPLC) has been obtained. The chromatography steps have been performed in a bind-and-elute mode.

Thus, another aspect of the current invention is a method for the purification of IFNα-2a comprising a sequence of three successive chromatography steps, whereby the first chromatography step is a hydrophobic charge induction chromatography step, the second chromatography step is an anion exchange chromatography step, and the third chromatography step is an hydrophobic charge induction chromatography step.

The IFNα-2a has also been purified for comparison with a different sequence of chromatography steps:

1) hydrophobic interaction chromatography (a-ii),
2) cation exchange chromatography (b-ii), and
3) hydrophobic interaction chromatography (c-iv).

After performing the purification method with the chromatography steps as outlined above a purity of more than 97% (determined by HPLC) has been obtained.

Thus, another aspect of the current invention is a method for the purification of IFNα-2a comprising a sequence of three successive chromatography steps, whereby the first chromatography step is a hydrophobic interaction chromatography, the second chromatography step is a cation exchange chromatography step, and the third chromatography step is an hydrophobic interaction chromatography.

PEGylated Interferon

The method according to the invention is not only applicable to non-glycosylated, recombinantly produced polypeptides, it is further more also suitable for the production of PEGylated, non-glycosylated polypeptides. For exemplary PEGylated interferon see e.g., EP 0 809 996.

Thus, another aspect of the current invention is a method for producing a non-glycosylated, PEGylated, heterologous polypeptide, which has been recombinantly produced in a prokaryotic cell comprising the following steps in the following order:

a) providing a non-glycosylated, heterologous polypeptide, which has been recombinantly produced in a prokaryotic cell,
b) a first chromatography step selected from
  i) hydrophobic charge induction chromatography,
  ii) hydrophobic interaction chromatography,
  iii) affinity chromatography, or
  iv) ion exchange chromatography,
c) a second chromatography step selected from
  i) anion exchange chromatography,
  ii) cation exchange chromatography,
  iii) hydroxylapatite chromatography, or
  iv) hydrophobic interaction chromatography,
d) a third chromatography step selected from
  i) hydrophobic charge induction chromatography,
  ii) anion exchange chromatography,
  iii) cation exchange chromatography, or
  iv) hydrophobic interaction chromatography,
whereby said non-glycosylated, heterologous polypeptide is obtained after PEGylation after step d).

Due to the different characteristics of different polypeptides, which are depending on its physical properties, such as e.g., the isoelectric point (Ip) or the distribution of surface exposed amino acid residues, not all chromatography methods are suited for all polypeptides. Therefore the following provisos apply to the method according to the invention:

the first chromatography step is an affinity chromatography or a hydrophobic charge induction chromatography in case of polypeptides capable of interacting with metal ligands,
the second chromatography step is not a hydroxylapatite chromatography step in case of polypeptides with an isoelectric point below 6.0,
the third chromatography step can be performed in flow-through mode with polypeptides having a low or high isoelectric point.

An exemplary PEGylated IFN is reported in EP 0 809 996.

For the production of the PEGylated IFN a sequence of three chromatography steps according to the method according to the invention have been performed. The sequences comprises the chromatography steps:

1) hydrophobic interaction chromatography (b-ii),
2) cation exchange chromatography (c-ii), and
3) anion exchange chromatography (d-ii), and after step 3) the purified non-glycosylated and non-PEGylated IFN is PEGylated.

The starting material had a purity of 58% (determined by HPLC). After performing the purification method according to the invention with the chromatography steps as outlined above a purity of more than 90% (determined by HPLC) has been obtained. All the chromatography steps have been performed in a bind-and-elute mode.

To show the versatility of the production method according to the invention also with PEGylated polypeptides the IFN has also been purified prior to PEGylation with a further sequence of chromatography steps according to the method according to the invention:

1) metal affinity chromatography (b-iii),
2) cation exchange chromatography (c-ii), and
3) anion exchange chromatography (d-ii), and after step 3) the purified non-glycosylated not-glycosylated and non-PEGylated PEGylated IFN is PEGylated.

After performing the purification method according to the invention with the chromatography steps as outlined above a purity of more than 90% (determined by HPLC) has been obtained. All the chromatography steps have been performed in a bind-and-elute mode.

Thus, another aspect of the current invention is a method for the production of a PEGylated IFNα-2a comprising a sequence of three successive chromatography steps whereby the first chromatography step is selected from hydrophobic interaction chromatography or metal affinity chromatography, the second chromatography step is a cation exchange chromatography, and the third chromatography step is an anion exchange chromatography and wherein after the third chromatography step the purified non-glycosylated and non-PEGylated IFN is PEGylated.

The production of PEGylated IFN has also been performed for comparison with a different sequence of three chromatography steps:

1) hydrophobic interaction chromatography (b-ii),
2) cation exchange chromatography (c-ii), and
3) hydrophobic charge induction chromatography (d-i), and after step 3) the purified non-glycosylated and non-PEGylated IFN is PEGylated.

After performing the purification method with the chromatography steps as outlined above a purity of 89% (determined by HPLC) has been obtained.

Thus, another aspect of the current invention is a method for the production of PEGylated interferon, especially IFNα-2a, comprising a sequence of three successive chromatography steps whereby the first chromatography step is hydrophobic interaction chromatography, the second chromatography step is a cation exchange chromatography, and the third chromatography step is an hydrophobic charge induction chromatography and wherein after the third chromatography step the purified non-glycosylated and non-PEGylated IFN is PEGylated.

*Escherichia*, *Salmonella*, *Streptomyces* or *Bacillus* are, for example, suitable as prokaryotic host organisms. In one embodiment is the prokaryotic cell an *E. coli* cell. Preferably the *E. coli* cell is an *E. coli* XL1-blue cell, or an *E. coli* BL21(DE3) cell, or an *E. coli* K-12 cell. In another embodiment is the non-glycosylated, heterologous polypeptide selected from growth factor agonists or antagonists, or interferons or interferon variants.

Another aspect of the current invention is a method for the recombinant production of a non-glycosylated heterologous polypeptide in a prokaryotic cell, characterized in that said method comprises the following steps:

a) cultivating a prokaryotic cell comprising a nucleic acid encoding said heterologous polypeptide under conditions suitable for the expression of said heterologous polypeptide,
b) recovering said heterologous polypeptide from the culture medium or the prokaryotic cells,
c) purifying said heterologous polypeptide with a method comprising the following steps in the following order:

α) a first chromatography step selected from
  i) hydrophobic charge induction chromatography,
  ii) hydrophobic interaction chromatography,
  iii) affinity chromatography, or
  iv) ion exchange chromatography,
β) a second chromatography step selected from
  i) anion exchange chromatography,
  ii) cation exchange chromatography,
  iii) hydroxylapatite chromatography, or
  iv) hydrophobic interaction chromatography, or
  v) hydrophobic charge induction chromatography,
γ) a third chromatography step selected from
  i) hydrophobic charge induction chromatography,
  ii) anion exchange chromatography,
  iii) cation exchange chromatography, or
  iv) hydrophobic interaction chromatography.

In one embodiment is the non-glycosylated heterologous polypeptide obtained after step c). Due to the different characteristics of different polypeptides, which are depending on its physical properties, such as e.g. the isoelectric point (Ip) or the distribution of surface exposed amino acid residues, not all chromatography methods are suited for all polypeptides. Therefore the following provisos apply to the method according to the invention:

the first chromatography step is an affinity chromatography or a hydrophobic charge induction chromatography in case of polypeptides capable of interacting with metal ligands,
the second chromatography step is not a hydroxylapatite chromatography step in case of polypeptides with an isoelectric point below 6.0,
the third chromatography step can be performed in flow-through mode with polypeptides having a low or high isoelectric point.

The term "under conditions suitable" as used within this application denotes conditions which are used for the cultivation of a cell expressing a polypeptide and which are known to or can easily be determined by a person skilled in the art. It is known to a person skilled in the art that these conditions may vary depending on the type of cell cultivated and type of polypeptide expressed. In general the cell is cultivated at a temperature, e.g., between 20° C. and 40° C., and for a period of time sufficient to allow effective production, e.g., for of from 4 to 28 days.

In one embodiment said chromatographic steps are performed in bind and elute mode. The term "bind and elute mode" as used in the current invention denotes an operation mode of a purification method, in which a solution containing a substance of interest to be purified is brought in contact with a stationary phase, preferably a solid phase, whereby the substance of interest binds to the stationary phase. As a result the substance of interest is retained on the stationary phase whereas substances not of interest are removed with the flow-through or the supernatant. The substance of interest is afterwards optionally after a washing step eluted from the stationary phase in a second step and thereby recovered from the stationary phase with an elution solution.

The term "PEGylating" means the formation of a covalent linkage of a (polyethylene)glycol residue at the N-terminus of the polypeptide and/or an internal lysine residue. PEGylation of proteins is widely known in the state of the art and reviewed by, for example, Veronese, F. M., Biomaterials 22 (2001) 405-417. PEG can be linked using different functional groups and polyethylene glycols with different molecular weight, linear and branched PEGs as well as different linking groups (see also Francis, G. E., et al., Int. J. Hematol. 68 (1998) 1-18; Delgado, C., et al., Crit. Rev.

Ther. Drug Carrier Systems 9 (1992) 249-304). Activated PEG derivatives are known in the art and are described in, for example, Morpurgo, M., et al., J. Bioconjug. Chem. 7 (1996) 363-368, for PEG-vinylsulfone. Linear chain and branched chain PEG species are suitable for the preparation of the PEGylated fragments. Examples of reactive PEG reagents are iodo-acetyl-methoxy-PEG, or methoxy-PEG-vinylsulfone.

In one embodiment of the methods according to the current invention is the content of endotoxins, and/or *E. coli* DNA, and/or *E. coli* cell proteins reduced in the polypeptide solution obtained after the third chromatography step compared to the content prior to the first chromatography step.

In another embodiment is the method according to the invention a method for the recombinant production of a non-glycosylated heterologous polypeptide in a prokaryotic cell via inclusion bodies, whereby the method comprises the following steps:
  a) cultivating a prokaryotic cell comprising a nucleic acid encoding said heterologous polypeptide under conditions suitable for the expression of said heterologous polypeptide and formation of inclusion bodies containing said heterologous polypeptide,
  b) recovering said inclusion bodies from the prokaryotic cells,
  c) solubilizing and renaturating said heterologous polypeptide from said inclusion bodies,
  d) purifying said heterologous polypeptide with a method according to the first aspect of the current invention.

In one embodiment is the non-glycosylated heterologous polypeptide obtained after step d). Inclusion bodies are found in the cytoplasm and contain the expressed polypeptide in an aggregated form insoluble in water. Usually, such proteins of inclusion bodies are in a denatured form (e.g., randomly linked disulfide bridges). These inclusion bodies are separated from other cell components, for example by centrifugation after cell lysis. According to the invention, the inclusion bodies are washed under denaturing conditions. Such denaturing agents are well known in the state of the art and are, for example, highly concentrated solutions of guanidinium hydrochloride (e.g., about 6 mol/l) or urea (e.g., about 8 mol/l). The denaturing agent is preferably used as a buffered solution. After washing, the inclusion bodies are solubilized.

The term "PEGylation" means a covalent linkage of a poly(ethylene glycol) residue at the N-terminus of the polypeptide and/or an internal lysine residue. PEGylation of proteins is widely known in the state of the art and reviewed by, for example, Veronese, F. M., Biomaterials 22 (2001) 405-417. PEG can be linked using different functional groups and polyethylene glycols with different molecular weight, linear and branched PEGs as well as different linking groups (see also Francis, G. E., et al., Int. J. Hematol. 68 (1998) 1-18; Delgado, C., et al., Crit. Rev. Ther. Drug Carrier Systems 9 (1992) 249-304). PEGylation can be performed in aqueous solution with PEGylation reagents as described, for example, in WO 00/44785, in one embodiment by using NHS-activated linear or branched PEG molecules of a molecular weight between 5 kDa and 40 kDa. PEGylation can also be performed at the solid phase according to Lu, Y., et al., Reactive Polymers 22 (1994) 221-229. Not randomly, N-terminally PEGylated polypeptide can also be produced according to WO 94/01451.

Activated PEG derivatives are known in the art and are described in, for example, Morpurgo, M., et al., J. Bioconjug. Chem. 7 (1996) 363-368, for PEG-vinylsulfone. Linear chain and branched chain PEG species are suitable for the preparation of the PEGylated fragments. Examples of reactive PEG reagents are iodo-acetyl-methoxy-PEG, or methoxy-PEG-vinylsulfone (m is preferably an integer from about 450 to about 900 and R is a $C_1$- to $C_6$-alkyl, linear or branched, having one to six carbon atoms such as methyl, ethyl, isopropyl, etc, whereby in one embodiment R=methyl):

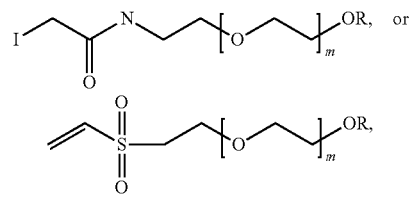

The use of these iodo-activated substances is known in the art and described e.g. by Hermanson, G. T., in Bioconjugate Techniques, Academic Press, San Diego (1996) p. 147-148.

In one embodiment is the PEG species an activated PEG ester, e.g., N-hydroxysuccinimidyl propionate, or N-hydroxysuccinimidyl butanoate, or N-hydroxysuccinimides such as PEG-NHS (Monfardini, C., et al., Bioconjugate Chem. 6 (1995) 62-69). In one embodiment the activated N-hydroxysuccinimide ester is

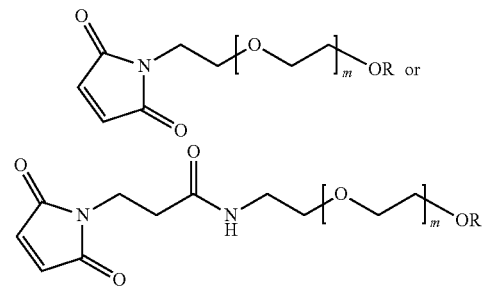

using alkoxy-PEG-N-hydroxysuccinimide, such as methoxy-PEG-N-hydroxysuccinimide (MW 30000; Shearwater Polymers, Inc.), wherein R and m are as defined above. In one embodiment the PEG species is the N-hydroxysuccinimidyl ester of methoxy poly(ethylene glycol)-butyric acid. The term "alkoxy" refers to an alkyl ether group in which the term 'alkyl' means a straight-chain or branched-chain alkyl group containing a maximum of four carbon atoms, such as methoxy, ethoxy, n-propoxy and the like, preferably methoxy.

One aspect of the invention is a method for the purification of a non-glycosylated, heterologous polypeptide, which has been recombinantly produced in a prokaryotic cell, characterized in that said method comprises the following steps in the following order:
  a) a first chromatography step selected from
    i) hydrophobic charge induction chromatography,
    ii) hydrophobic interaction chromatography,
    iii) affinity chromatography, or
    iv) ion exchange chromatography,
  b) a second chromatography step selected from
    i) anion exchange chromatography,
    ii) cation exchange chromatography,
    iii) hydroxylapatite chromatography, or
    iv) hydrophobic interaction chromatography, or
    v) hydrophobic charge induction chromatography, c) a third chromatography step selected from
   i) hydrophobic charge induction chromatography,
   ii) anion exchange chromatography,
   iii) cation exchange chromatography, or
   iv) hydrophobic interaction chromatography,
whereby
   said first chromatography step is an affinity chromatography or a hydrophobic charge induction chromatography in case of polypeptides capable of interacting with metal ligands,
   said second chromatography step is not a hydroxylapatite chromatography step in case of polypeptides with an isoelectric point below 6.0,
   said third chromatography step can be performed in flow-through mode with polypeptides having a low or high isoelectric point,
and with the proviso that the combination of three chromatographic steps is not
   affinity chromatography, ion exchange chromatography and hydrophobic interaction chromatography,
   hydrophobic interaction chromatography, cation exchange chromatography and anion exchange chromatography,
   cation exchange chromatography, anion exchange chromatography and hydrophobic interaction chromatography,
   cation exchange chromatography, hydrophobic interaction chromatography and cation exchange chromatography,
   anion exchange chromatography, hydrophobic interaction chromatography and hydrophobic interaction chromatography.

In one embodiment of the method according to the invention is the non-glycosylated heterologous polypeptide obtained after the third chromatography step.

The term "comparable" as used within this application denotes that two results are within 10% of each other. For example, a purity of 90% and a purity of 95% are comparable as 95% is within 10% of a purity of 90% (90%+10% of 90%=90%+9%=99%).

The following examples, references, and figures are provided to aid the understanding of the present invention, the true scope of which is set forth in the appended claims. It is understood that modifications can be made in the procedures set forth without departing from the spirit of the invention.

EXAMPLES

Material and Methods

Figure 1A:
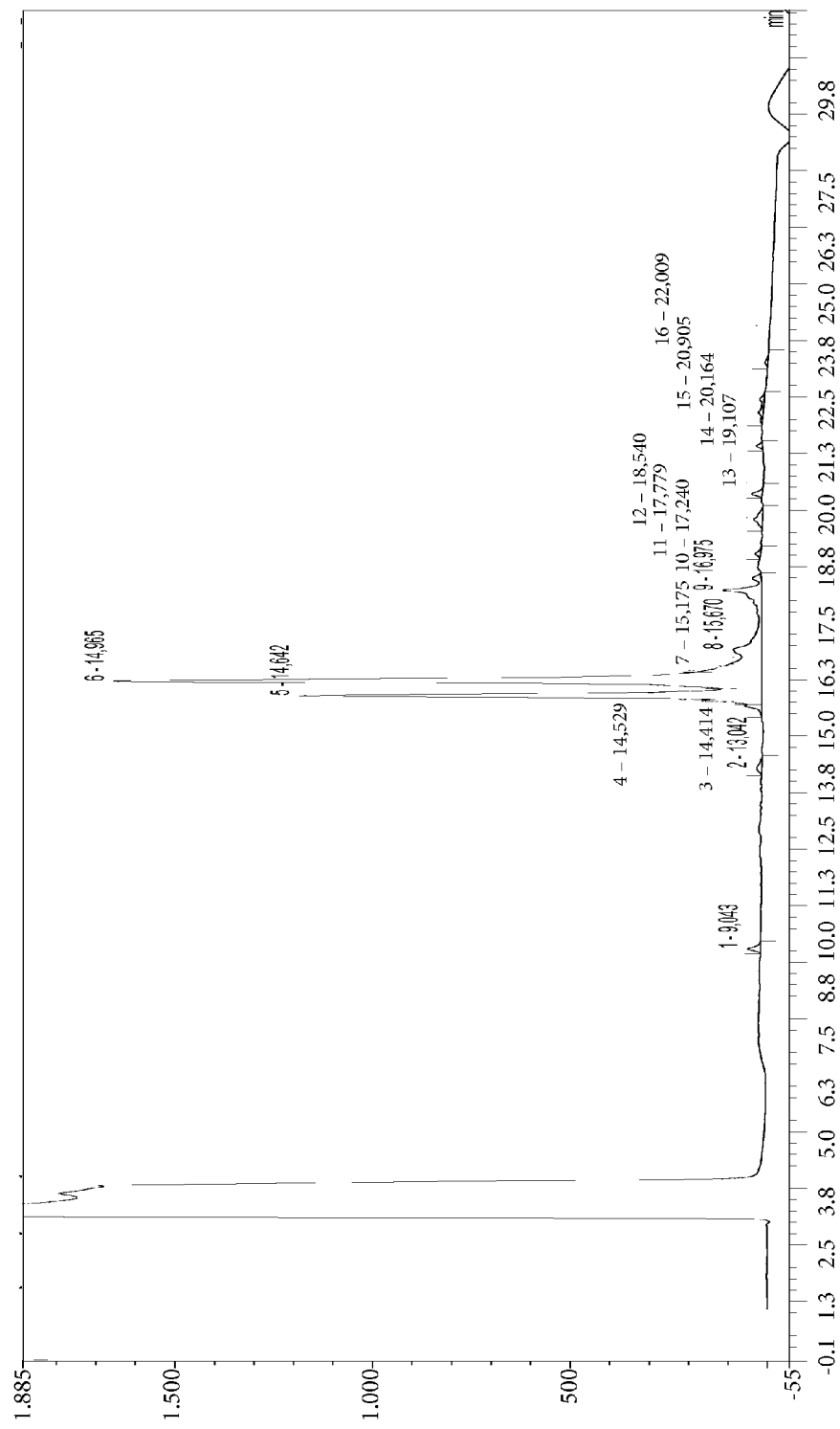
FIG. 1 Reversed Phase HPLC chromatogram of the IGF-1 agonist before (A) and after (B) the first HCIC.

If not otherwise indicated have the different chromatography methods been performed according to the chromatography material manufacturer's manual.

Recombinant DNA Techniques:

Standard methods were used to manipulate DNA as described in Sambrook, J., et al., Molecular cloning: A laboratory manual; Cold Spring Harbor Laboratory Press, Cold Spring Harbor, N.Y., 1989. The molecular biological reagents were used according to the manufacturer's instructions.

Protein Determination:

Protein concentration was determined by determining the optical density (OD) at 280 nm, with a reference wavelength of 320 nm, using the molar extinction coefficient calculated on the basis of the amino acid sequence.

Size-Exclusion-HPLC:

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 minutes at room temperature. The chromatograms were integrated manually with Chromeleon (Dionex, Idstein, Germany).

Reversed Phase HPLC (RP-HPLC):

The purity is analyzed by RP-HPLC. The assay is performed on a Poroshell column using an acetonitrile/aqueous TFA gradient. The elution profile is monitored as UV absorbance at 215 nm. The percentages of the eluted substances are calculated based upon the total peak area of the eluted proteins.

DNA-Threshold-System:

See e.g., Merrick, H., and Hawlitschek, G., Biotech Forum Europe 9 (1992) 398-403.

Host Cell Protein Determination:

The walls of the wells of a micro titer plate are coated with a mixture of serum albumin and Streptavidin. A goat derived polyclonal antibody against HCP is bound to the walls of the wells of the micro titer plate. After a washing step different wells of the micro titer plate are incubated with a HCP calibration sequence of different concentrations and sample solution. After the incubation not bound sample material is removed by washing with buffer solution. For the detection the wells are incubated with an antibody peroxidase conjugate to detect bound host cell protein. The fixed peroxidase activity is detected by incubation with ABTS and detection at 405 nm.

General Method for the Isolation, Solubilization and Renaturation of Inclusion Bodies:

In addition to the method performed in the cited literature can the preparation of inclusion bodies e.g., be performed according to the method by Rudolph et al. (Rudolph et al., Folding Proteins, In: T. E. Creighton (ed.): Protein function: A Practical Approach, 57 (1996)). The inclusion bodies were stored at −70° C. Solubilization of the inclusion bodies can likewise be performed according the method by Rudolph et al. (Rudolph et al., Folding Proteins, In: T. E. Creighton (ed.): Protein function: A Practical Approach, 57 (1996)).

Example 1

Purification of an IGF-1 Agonist

The polypeptide was expressed in E. coli. The polypeptide is first applied to a HCIC column, then to a hydroxylapatite column and finally to a second HCIC column.

The chromatographic conditions were as follows:
1$^{st}$ Column:
Resin: HCIC with MEP-Hypercel (Pall Corporation, USA) as single step elution
Loading: 10 mg polypeptide per ml of column volume
Buffer A: 25 mM tris(hydroxymethyl)amino methane buffer, adjusted to pH 9.0
Buffer B: 10 mM sodium acetate buffer, adjusted to pH 5.0

The solution containing the IGF-1 agonist was applied in a first step to a column containing a hydrophobic charge induction chromatography material (MEP-Hypercel from Pall Corporation).

Figure 1B:
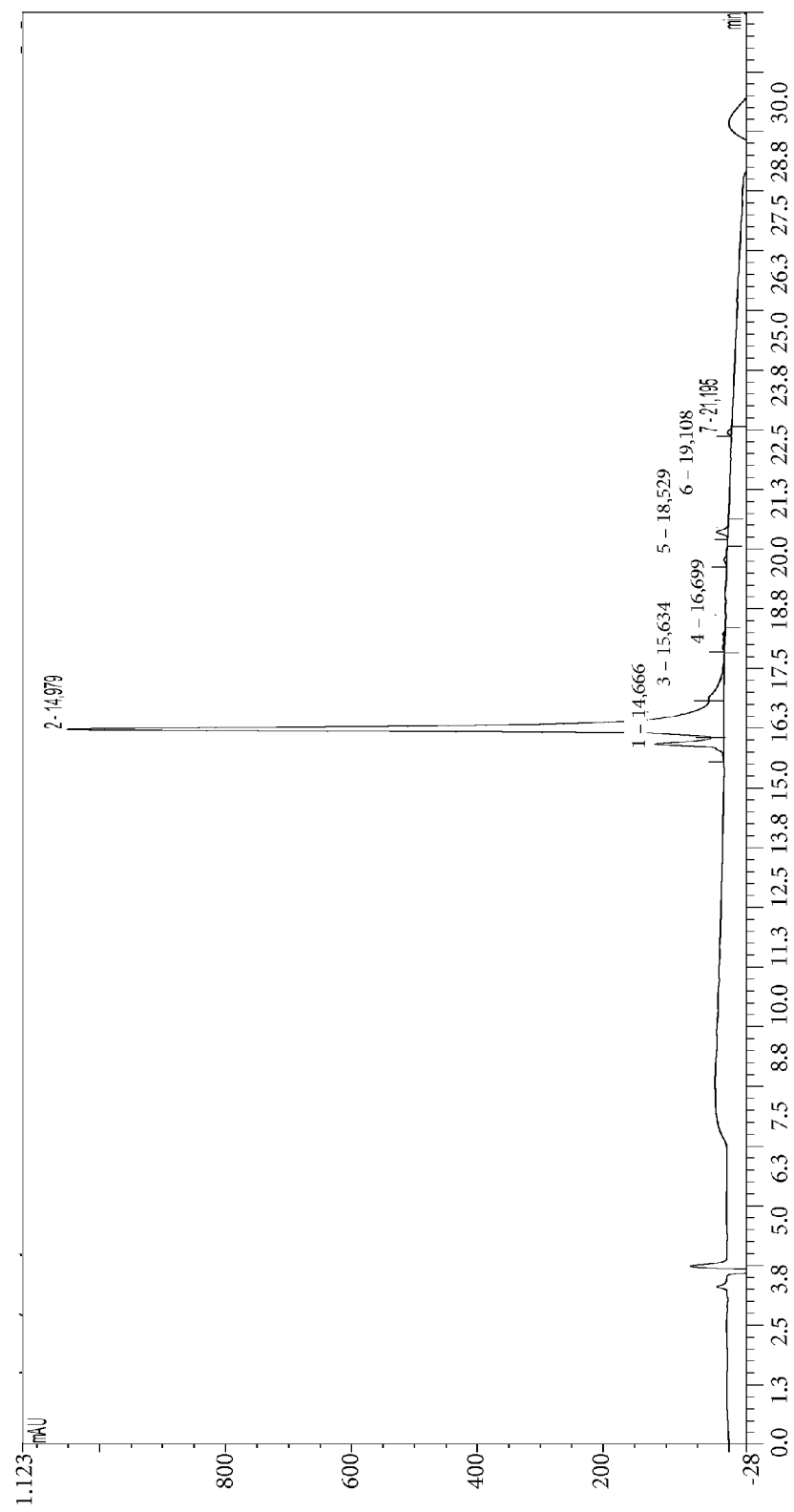

In FIG. 1 the reversed phase chromatogram of the IGF-1 agonist before and after HCIC is presented.

2$^{nd}$ Column:
Resin: Hydroxylapatite chromatography (Biorad Laboratories, USA)
Loading: 6.5 mg polypeptide per ml of column volume
Buffer A: 5 mM potassium phosphate buffer, adjusted to pH 6.5
Buffer B: 10 mM MES buffer supplemented with 1 M sodium chloride, adjusted to pH 6.5

Figure 2A:
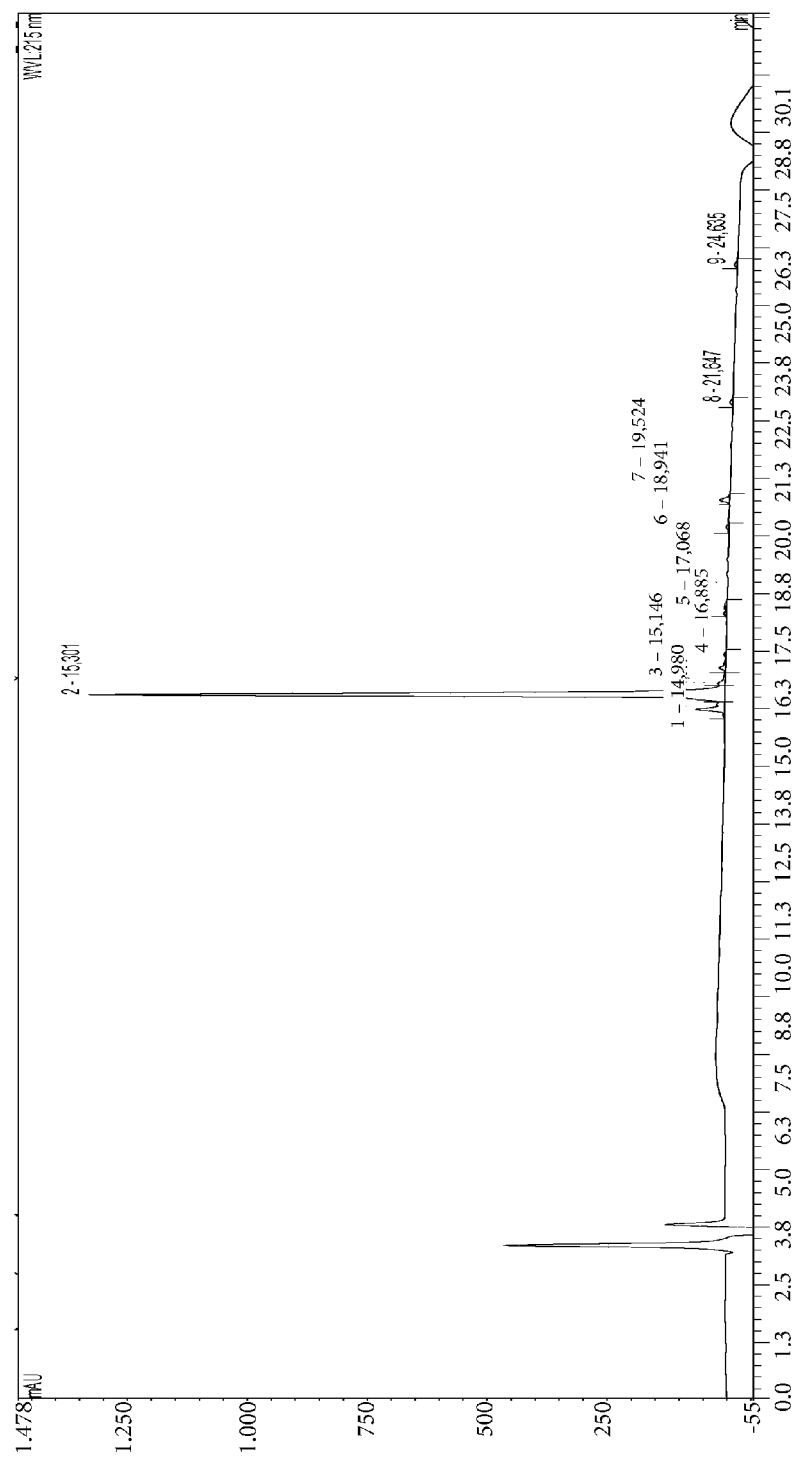
FIG. 2 Reversed Phase HPLC chromatogram of the IGF-1 agonist before (A) and after (B) the hydroxylapatite chromatography step.
Figure 2B:
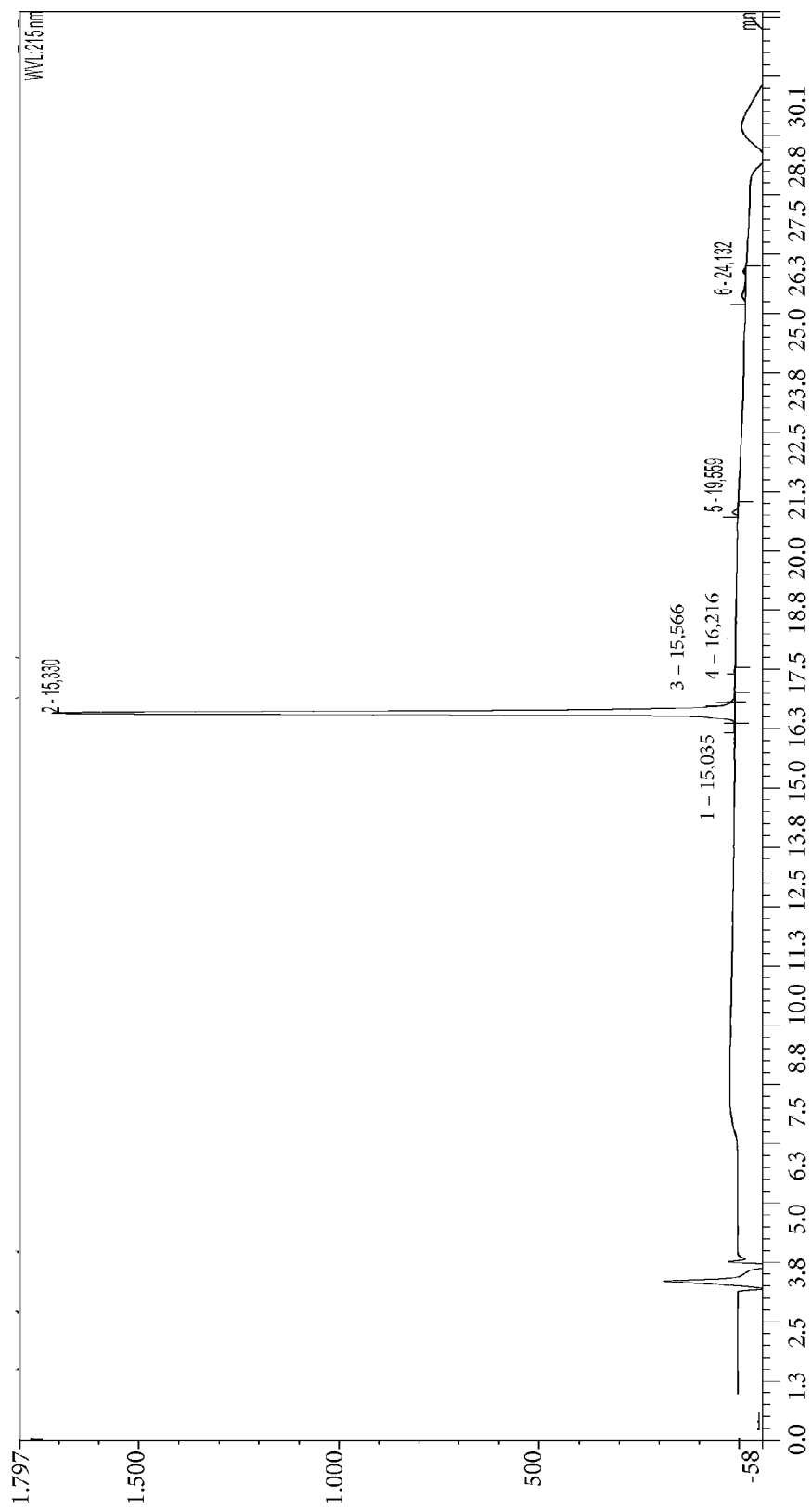

FIG. 2 presents the reversed phase chromatogram before and after the hydroxylapatite chromatography step.

3$^{rd}$ Column:
Resin: HCIC with HEA-Hypercel (Pall Corporation, USA)
Loading: 20 mg polypeptide per ml of column volume
Buffer A: 20 mM sodium acetate buffer, adjusted to pH 4.0

Figure 3A:
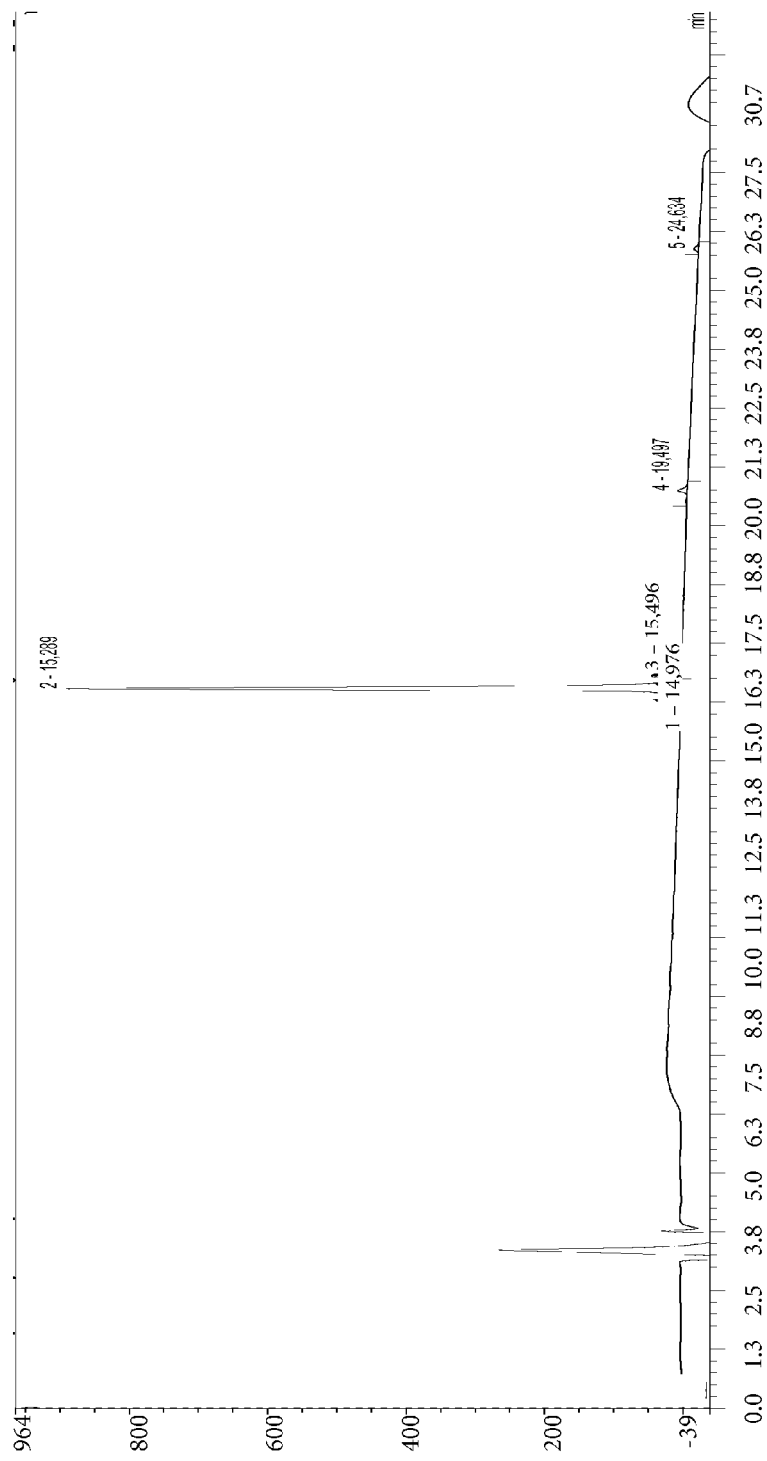
FIG. 3 Reversed Phase HPLC chromatogram of the IGF-1 agonist before (A) and after (B) the second HCIC.
Figure 3B:
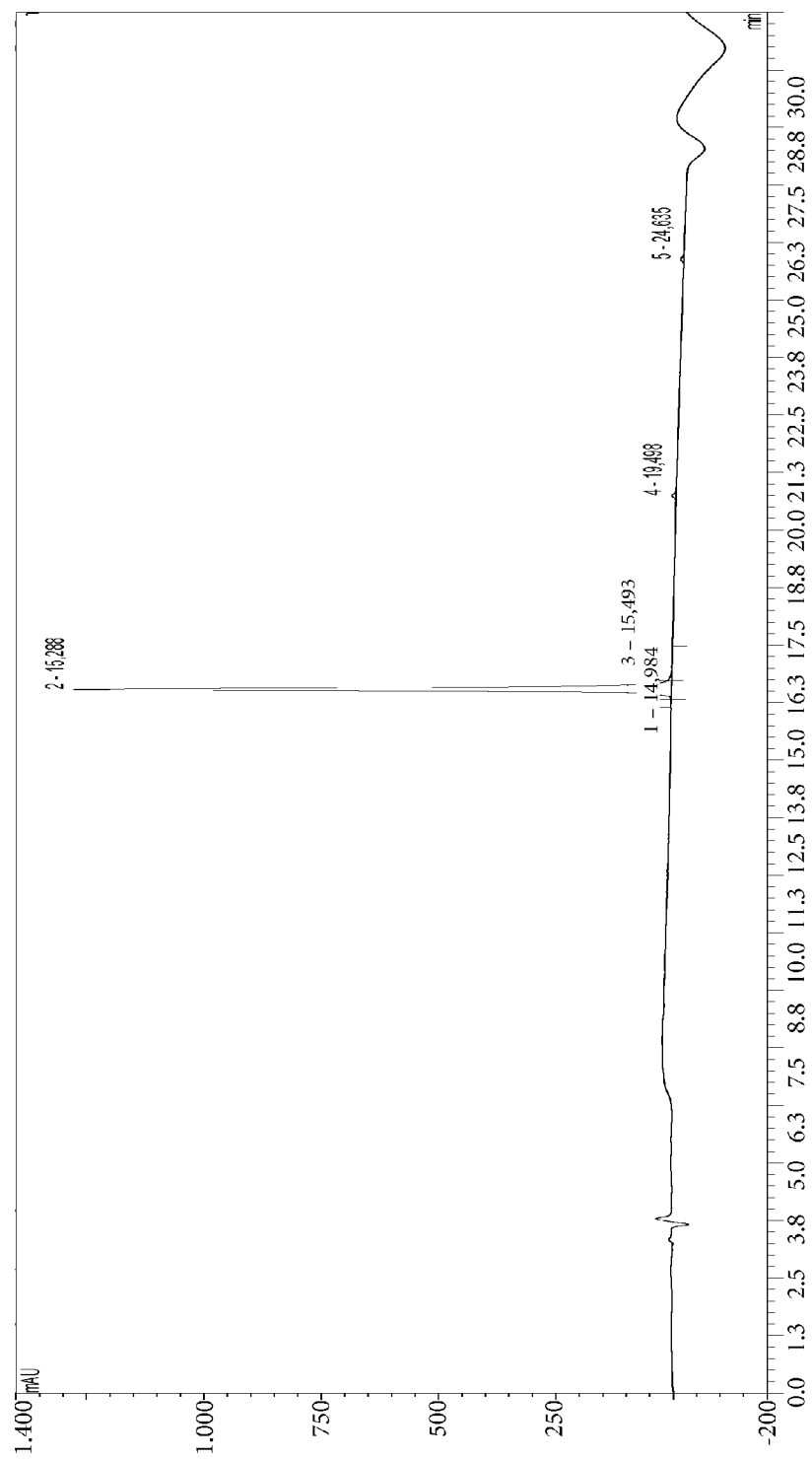

FIG. 3 presents the reversed phase chromatogram before and after the second HCIC step.

| Column | Yield [%] | Purity determined by HPLC [%] |
|---|---|---|
| Start | | 49.2 |
| HCIC step | 15.7 | 86.6 |
| Hydroxylapatite chromatography step | 62.5 | 97.0 |
| HCIC step | 94.2 | 97.7 |

Example 2

Purification of IGF-1 Agonist—Comparative Example to Example 1

The polypeptide is first applied to a HIC column, followed by a cation exchange chromatography and finally to an anion exchange chromatography operated in flow-through mode.
1$^{st}$ Column:
Resin: HIC with Super Butyl Toyopearl (Tosoh Haas Corp., USA)
Loading: 5 mg polypeptide per ml of column volume
Buffer A: 50 mM potassium phosphate buffer supplemented with 1M potassium chloride, adjusted to pH 8.0
Buffer B: 2-propanol 5-10% (w/v), adjusted to pH 4.0

Elution was performed with a linear gradient over 30 column volumes from 0% (v/v) to 100% (v/v) of buffer B.

Figure 4A:
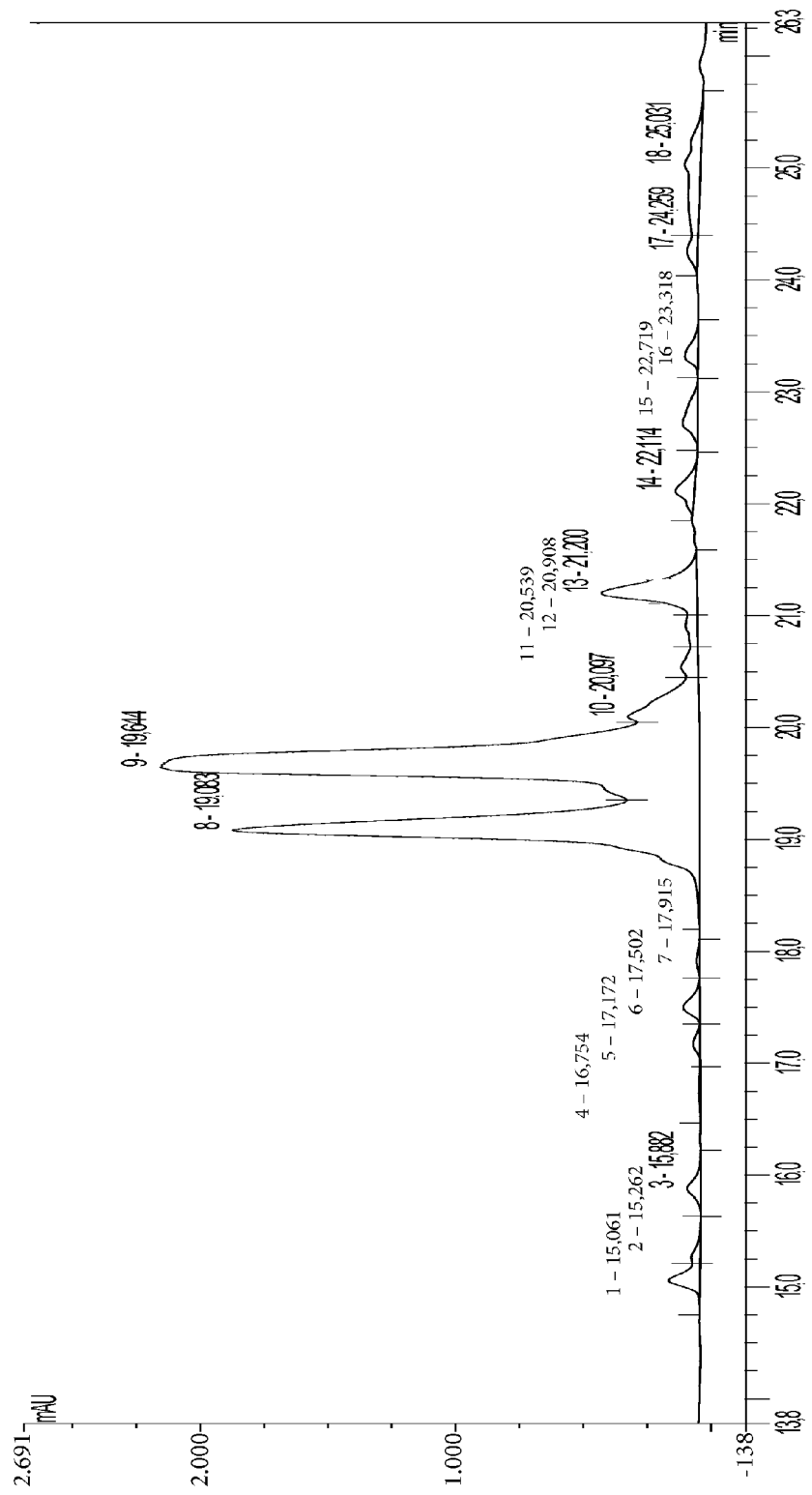
FIG. 4 Reversed Phase HPLC chromatogram of the IGF-1 agonist before (A) and after (B) the HIC.

FIG. 4 presents the reversed phase chromatogram before and after the HIC step.

2$^{nd}$ Column:
Resin: Cation exchange chromatography with CM-Sepharose FF (GE-Healthcare, USA)
Loading: 4.1 mg polypeptide per ml of column volume
Buffer A: 50 mM acetic acid, adjusted to pH 5.8
Buffer B: 100 mM tris(hydroxymethyl)amino methane buffer supplemented with 1 M sodium chloride, adjusted to pH 9.5

Elution was performed as follows: change to 15% (v/v) buffer B at the start, maintaining 15% (v/v) buffer B for 5 column volumes, afterwards a linear gradient to 55% (v/v) buffer B over 20 column volumes, and finally maintaining 55% (v/v) buffer B for 10 column volumes.

Figure 5A:
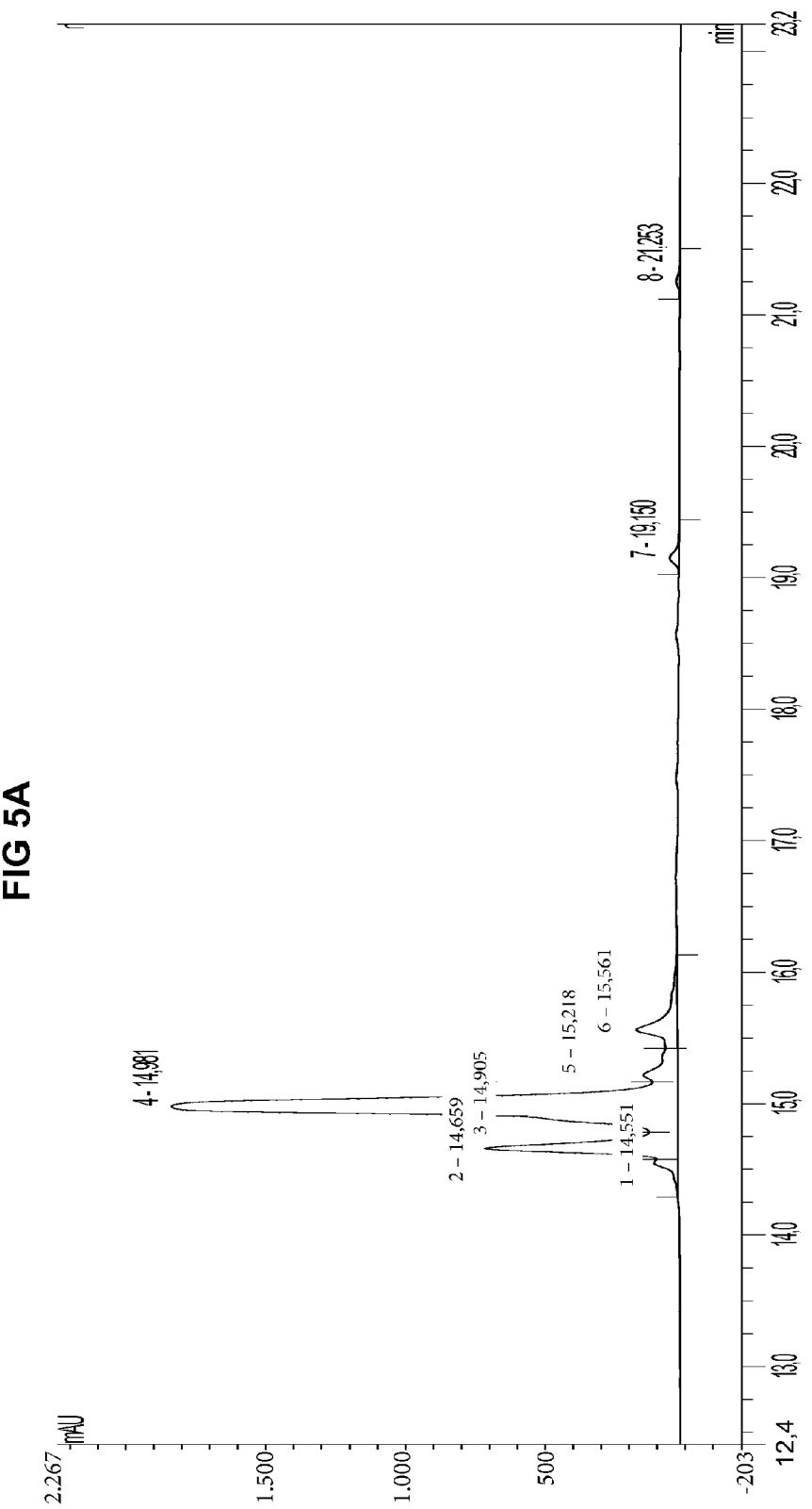
FIG. 5 Reversed Phase HPLC chromatogram of the IGF-1 agonist before (A) and after (B) the cation exchange chromatography step.

FIG. 5 presents the reversed phase chromatogram before and after the cation exchange chromatography step.

3$^{rd}$ Column:
Resin: Anion exchange chromatography with Q-Sepharose in flow-through mode (GE-Healthcare, USA)
Loading: 20 mg polypeptide per ml of column volume
Buffer A: 25 mM tris(hydroxymethyl)amino methane buffer, adjusted to pH 9.5
Buffer B: 10 mM acetic acid (pH 3.6)

Figure 6A:
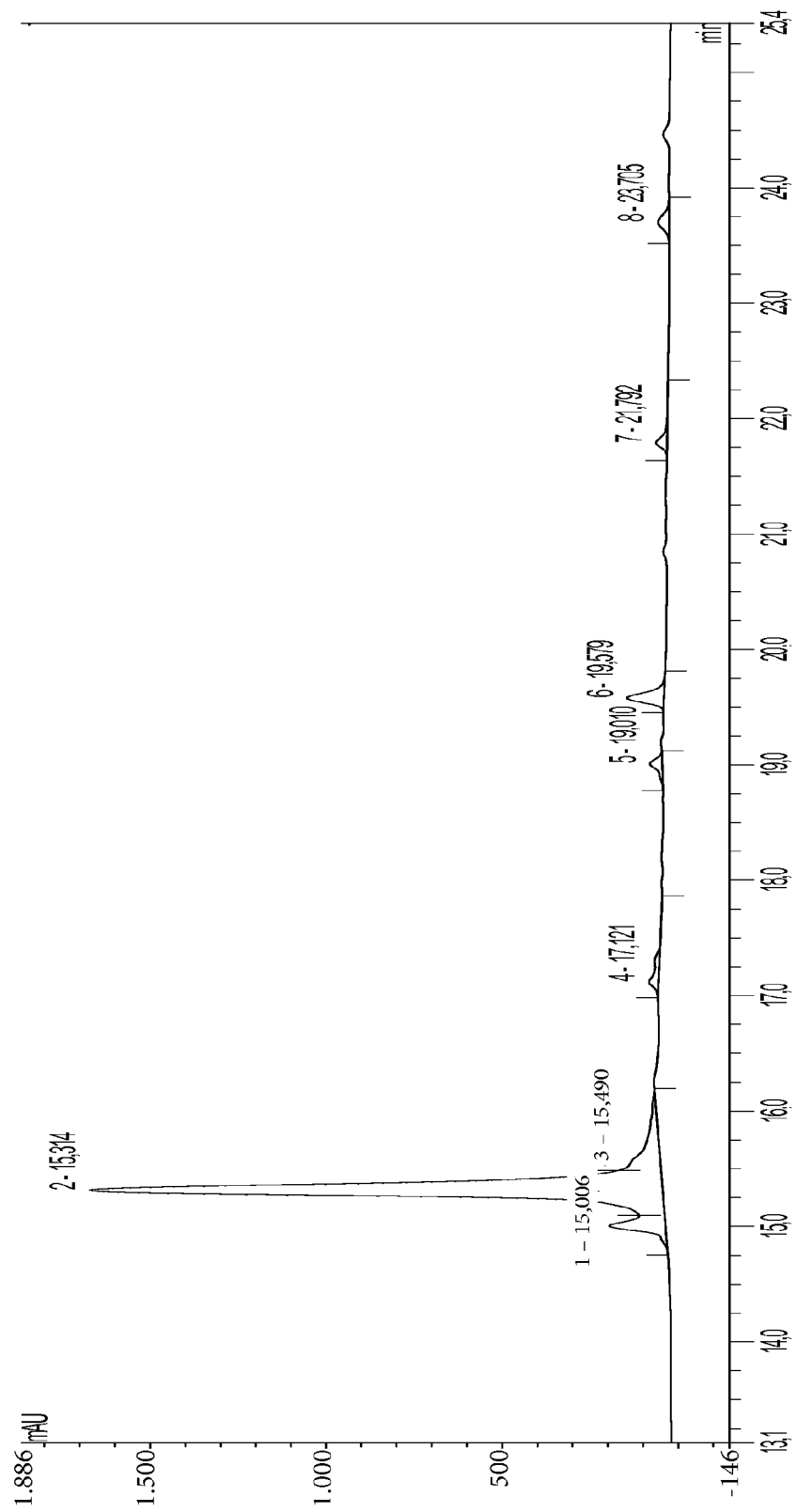
FIG. 6 Reversed Phase HPLC chromatogram of the IGF-1 agonist before (A) and after (B) the anion exchange chromatography step.
Figure 6B:
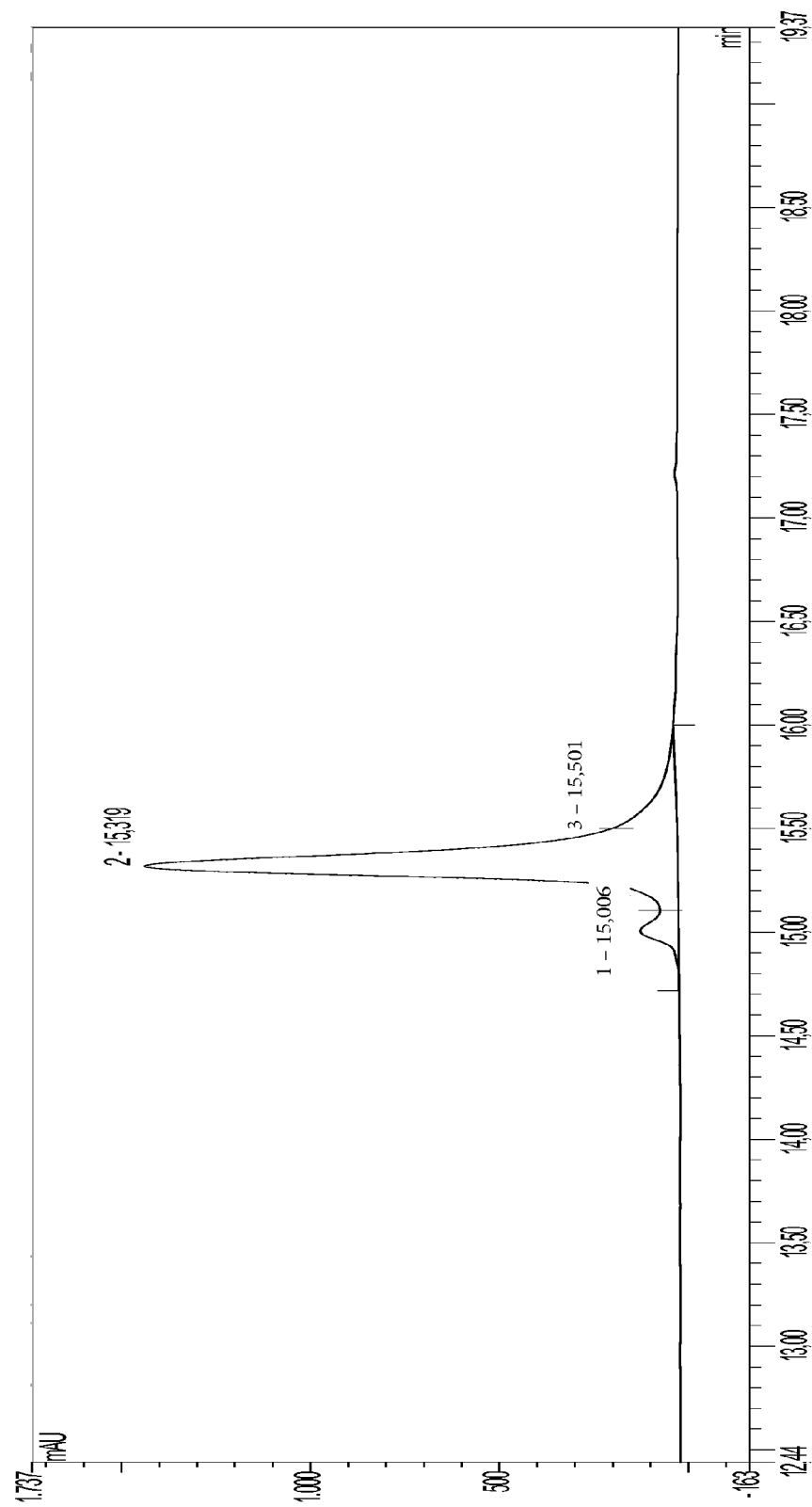

FIG. 6 presents the reversed phase chromatogram before and after the anion exchange chromatography step.

| Column | Yield [%] | Purity determined by HPLC [%] |
|---|---|---|
| Start | | 49.6 |
| HIC step | 16.7 | approx. 90 |
| Cation exchange chromatography step | 14.2 | 90.1 |
| Anion exchange chromatography step | 93.8 | 97.0 |

Example 3

Purification of Interferon

The polypeptide is first applied to a HIC column, then to an anion exchange column and finally to a cation exchange column.

The chromatographic conditions were as follows:
1$^{st}$ Column:
Resin: HIC with Butyl Sepharose (GE-Healthcare, USA) as single step elution
Loading: 8 mg polypeptide per ml of column volume
Buffer A: 20 mM potassium phosphate buffer, adjusted to pH 8.0
2$^{nd}$ Column:
Resin: Anion exchange chromatography with Q-Sepharose FF (GE-Healthcare, USA)
Loading: 1.5 mg polypeptide per ml of column volume
Buffer A: 30 mM ammonium acetate, adjusted to pH 5.9
Buffer B: 1.8 mM ammonium acetate, adjusted to pH 3.5

Elution was performed as follows: change to 15% (v/v) buffer B at the start, maintaining 15% (v/v) buffer B for 3 column volumes, and afterwards a linear gradient to 90% (v/v) buffer B over 37.5 column volumes.

3$^{rd}$ Column:
Resin: Cation exchange chromatography with SP-Sepharose as single step elution Loading: 2.84 mg polypeptide per ml of column volume
Buffer A: 50 mM borate buffer supplemented with 250 mM sodium chloride, adjusted to pH 9.0

| Column | Yield [%] | Purity determined by HPLC [%] |
|---|---|---|
| Start | | 48.8 |
| HIC step | 13.4 | 69.3 |
| Anion exchange chromatography step | 55.0 | 97.5 |
| Cation exchange chromatography step | 89.5 | Approx. 100 |

Example 4

Purification of Interferon—Comparative Example to Example 3

The polypeptide is first applied to a HIC column, then to a cation exchange column and finally to an anion exchange column.

The chromatographic conditions were as follows:
$1^{st}$ Column:
Resin: HIC with Butyl Sepharose (GE-Healthcare, USA)
Loading: 8 mg polypeptide per ml of column volume
Buffer A: 20 mM potassium phosphate buffer supplemented with 2 m potassium chloride, adjusted to pH 8.0
Buffer B: 20 mM potassium phosphate buffer, adjusted to pH 8.0
$2^{nd}$ Column:
Resin: Cation exchange chromatography with CM Toyopearl (Tosoh Hass Corp., USA)
Loading: 5 mg polypeptide per ml of column volume
Buffer A:
  equilibration: 75 mM sodium acetate, adjusted to pH 4.0
  wash: 15 mM sodium acetate, adjusted to pH 5.5
Buffer B: 30 mM sodium acetate, adjusted to pH 7.0
$3^{rd}$ Column:
Resin: Anion exchange chromatography with Q-Sepharose
Loading: 3 mg polypeptide per ml of column volume
Buffer A: 30 mM ammonium acetate buffer, adjusted to pH 6.8
Buffer B:
  1) 25 mM ammonium acetate, adjusted to pH 6.5
  2) 1.8 mM ammonium acetate supplemented with 3 mM acetic acid, adjusted to pH 4.5

| Column | Yield [%] | Purity determined by HPLC [%] |
|---|---|---|
| Start | | 58 |
| HIC step | 2.3 | 71.6 |
| Cation exchange chromatography step | 28.3 | 88.3 |
| Anion exchange chromatography step | 95.3 | 93.2 |

Example 5

Purification of Interferon—Comparative Example to Examples 3 and 4

The polypeptide is first applied to a metal chelating column, then to a cation exchange column and finally to an anion exchange column.

The chromatographic conditions were as follows:
$1^{st}$ Column:
Resin: Copper chelating Sepharose (GE-Healthcare, USA) as single step elution
Loading: 51 mg polypeptide per ml of column volume
Buffer A:
  equilibration: 300 mM guanidinium hydrochloride supplemented with 150 mM sodium chloride and 20 mM sodium phosphate buffer, adjusted to pH 6.45
  wash: 50 mM acetic acid supplemented with 100 mM sodium chloride, adjusted to pH 4.95
Buffer B: 50 mM acetic acid supplemented with 100 mM sodium chloride, adjusted to pH 3.9
$2^{nd}$ Column:
Resin: Cation exchange chromatography with CM Toyopearl (Tosoh Hass Corp., USA) as single step elution
Loading: 5 mg polypeptide per ml of column volume
Buffer A:
  equilibration: 75 mM sodium acetate, adjusted to pH 4.0
  wash: 15 mM sodium acetate, adjusted to pH 5.5
Buffer B: 30 mM sodium acetate, adjusted to pH 7.0
$3^{rd}$ Column:
Resin: Anion exchange chromatography with Q-Sepharose
Loading: 3 mg polypeptide per ml of column volume
Buffer A: 30 mM ammonium acetate buffer, adjusted to pH 6.8
Buffer B:
  1) 25 mM ammonium acetate, adjusted to pH 6.5
  2) 1.8 mM ammonium acetate supplemented with 3 mM acetic acid, adjusted to pH 4.5

Elution was performed as follows: change to 10% (v/v) buffer B at the start, maintaining 15% (v/v) buffer B for 3 column volumes, and afterwards a linear gradient to 90% (v/v) buffer B over 27.5 column volumes.

| Column | Yield [%] | Purity determined by HPLC [%] |
|---|---|---|
| Start | | 47.3 |
| Metal chelating chromatography step | 3.2 | 59.8 |
| Cation exchange chromatography step | 28.3 | 88.3 |
| Anion exchange chromatography step | 95.3 | 93.2 |

What is claimed is:

1. A method for purifying a non-glycosylated polypeptide, wherein the non-glycosylated polypeptide is interferon, the method comprising a sequence of three successive chromatography steps comprising
    a) a first chromatography step consisting of hydrophobic interaction chromatography;
    b) a second chromatography step consisting of anion exchange chromatography; and
    c) a third chromatography step consisting of cation exchange chromatography.

2. The method of claim 1, wherein the polypeptide is produced in a prokaryotic cell.

3. The method of claim 2, wherein the prokaryotic cell is an *E. coli* cell.

4. A method of PEGylating interferon, wherein the method comprises PEGylating the interferon purified by the method of claim 1.

5. A method for producing a purified non-glycosylated interferon produced in a prokaryotic cell, the method comprising a) cultivating a prokaryotic cell comprising a nucleic acid encoding the interferon under conditions suitable for expression of the interferon,
b) recovering the interferon from the culture medium or from the prokaryotic cells, and
c) purifying the interferon according to the method of claim 1.

6. A method for producing a purified non-glycosylated interferon from inclusion bodies produced in a prokaryotic cell, the method comprising
   a) cultivating a prokaryotic cell comprising a nucleic acid encoding the interferon under conditions suitable for expression of the interferon,
   b) recovering inclusion bodies from the prokaryotic cell,
   c) solubilizing and renaturing the interferon from the inclusion bodies, and
   d) purifying the interferon according to the method of claim 1.

7. The method of claim 1, wherein the polypeptide is interferon alpha-2a.

8. The method of claim 5, wherein the polypeptide is interferon alpha-2a.

9. The method of claim 6, wherein the polypeptide is interferon alpha-2a.

10. A method of PEGylating interferon alpha-2a, wherein the method comprises PEGylating the interferon alpha-2a purified by the method of claim 7.

\* \* \* \* \*